US011850048B2

(12) United States Patent
Gordon et al.

(10) Patent No.: US 11,850,048 B2
(45) Date of Patent: Dec. 26, 2023

(54) METHODS AND SYSTEMS FOR DETERMINING EMOTIONAL CONNECTIVITY USING PHYSIOLOGICAL MEASUREMENTS FROM CONNECTED DEVICES

(71) Applicant: LULULEMON ATHLETICA CANADA INC., Vancouver (CA)

(72) Inventors: Sian Elizabeth Gordon, Vancouver (CA); Sian Victoria Allen, Vancouver (CA); Todd James Smith, Vancouver (CA); Brandon Scott Jung, Vancouver (CA); Ellisa Kathleen Calder, Vancouver (CA); Navjot Kailay, Vancouver (CA); Kerem Dogurga, Vancouver (CA)

(73) Assignee: Lululemon Athletica Canada Inc., Vancouver (CA)

( * ) Notice: Subject to any disclaimer, the term of this patent is extended or adjusted under 35 U.S.C. 154(b) by 0 days.

(21) Appl. No.: 17/776,833

(22) PCT Filed: Nov. 13, 2020

(86) PCT No.: PCT/CA2020/051557
§ 371 (c)(1),
(2) Date: May 13, 2022

(87) PCT Pub. No.: WO2021/092701
PCT Pub. Date: May 20, 2021

(65) Prior Publication Data
US 2022/0409111 A1 Dec. 29, 2022

Related U.S. Application Data

(60) Provisional application No. 62/936,203, filed on Nov. 15, 2019.

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0002* (2013.01); *A61B 5/0004* (2013.01); *A61B 5/0816* (2013.01); *G16H 20/70* (2018.01)

(58) Field of Classification Search
None
See application file for complete search history.

(56) References Cited

U.S. PATENT DOCUMENTS

2011/0300847 A1* 12/2011 Quy ..................... H04W 4/00
                                                            455/419
2018/0193697 A1   7/2018 Burich et al.
2020/0008725 A1* 1/2020 Bach ..................... A61B 5/369

FOREIGN PATENT DOCUMENTS

EP          2108311 A1   10/2009

OTHER PUBLICATIONS

International Search Report and Written Opinion of International Application No. PCT/CA2020/051557 dated Jan. 6, 2021.
Daftari, J. et al., "Towards a Real-time Application to Reveal Entrainment Among People", 2012 IEEE International Conference on Communications (ICC), Jun. 15, 2012, pp. 6086-6090.
Hemakom, A. et al., "Quantifying Cooperation in Choir Singing: Respiratory and Cardiac Synchronisation", 2016 IEEE International Conference on Acoustics, Speech and Signal Processing (ICASSP), Mar. 25, 2016, pp. 719-723.
(Continued)

*Primary Examiner* — Catherine M Voorhees
*Assistant Examiner* — Elizabeth K So
(74) *Attorney, Agent, or Firm* — Norton Rose Fulbright Canada LLP; Maya Medeiros

(57) ABSTRACT

The disclosure provides methods and systems for determining an emotional fitness metrics for users. A physiological parameter of the user is measured during a group activity using at least one biosensor to acquire a measured signal. The measured signal of the user is compared to a measured signal for the physiological parameter of one or more additional users as measured when the one or more addi-
(Continued)

tional users perform the group activity. An emotional connectivity may be calculated based on a synchronicity of the measured signal of the user with the measured signal of the one or more additional users, as well as a cognitive appraisal metric, a resilience metric and an emotional fitness metric. Connectivity values for user pairings for a group activity can be computed based a synchronicity in a time-series correlation for the physiological parameters for permutations of the user pairings for the group activity.

10 Claims, 20 Drawing Sheets

(51) Int. Cl.
*G16H 20/70* (2018.01)
*A61B 5/08* (2006.01)

(56) References Cited

OTHER PUBLICATIONS

Rezaei, S., "Physiological Synchrony as Manifested in Dyadic Interactions", A thesis submitted in conformity with the requirements for the degree of Master of Applied Science Graduate Department of Institute of Biomaterials and Biomedical Engineering University of Toronto, 2013, pp. 1-40.

Quer, G. et al., "Heart rate wavelet coherence analysis to investigate group entrainment", Pervasive and Mobile Computing, 28 (2016), pp. 21-34, https://www.sciencedirect.com/science/article/abs/pii/S1574119215001844, Oct. 13, 2015 (Oct. 13, 2015).

Quer, G. et al., "Bliss Buzzer, a system to monitor health and stress with real-time feedback", SenSys '13: Proceedings of the 11th ACM Conference on Embedded Networked Sensor Systems, Article 82, pp. 1-2, http://dx.doi.org/10.1145/2517351.2517427, Nov. 2013 (Nov. 2013).

\* cited by examiner

|       | Beat-to-beat Heartrate | | | |
|-------|-------|-------|-------|-------|
| Time  | User 1 | User 2 | User 3 | User 4 |
| 0     | 64 | 55 | 68 | 80 |
| 1     | 61 | 56 | 67 | 68 |
| 2     | 61 | 55 | 67 | 69 |
| ...   | ... | ... | ... | ... |

FIG. 5A

|        | User 1 | User 2 | User 3 | User 4 |
|--------|--------|--------|--------|--------|
| User 1 | NA     | 0.867  | 0.874  | 0.913  |
| User 2 | 0.867  | NA     | 0.871  | 0.883  |
| User 3 | 0.874  | 0.871  | NA     | 0.887  |
| User 4 | 0.913  | 0.883  | 0.887  | NA     |

FIG. 5B

| User Pairing | | Cross-correlation |
|---|---|---|
| First User | Second User | |
| User 1 | User 4 | 0.913 |
| User 3 | User 4 | 0.887 |
| User 2 | User 4 | 0.883 |
| User 1 | User 3 | 0.874 |
| User 2 | User 3 | 0.871 |
| User 1 | User 2 | 0.867 |

FIG. 5C

| User | Area Under Curve | Number of Peaks | Meak Peak Height | Relative Mean Peak Height | Peak Weight | Resilience |
|---|---|---|---|---|---|---|
| User 1 | 42.5570 | 20 | 40.30000 | 28.38028 | 5.676056 | 242 |
| User 2 | 54.0360 | 16 | 38.37500 | 32.79915 | 5.247863 | 284 |
| User 3 | 45.0255 | 17 | 34.22222 | 27.59857 | 4.691756 | 211 |
| User 4 | 41.6680 | 21 | 33.22727 | 26.37085 | 5.537879 | 231 |

FIG. 7

Touch screen to begin

FIG. 10

TODAY, SEPTEMBER 26 / 45-MIN VINAYASA

Good afternoon

Sign In

* Email

* Password

SIGN IN

Not Registered?

CREATE ACCOUNT

FIG. 11

TODAY, SEPTEMBER 26 / 45-MIN VINAYASA

Welcome back, Sonya.

Thank you, calculating class results...

FIG. 14

TODAY, SEPTEMBER 26 / 45-MIN VINYASA

1500 Connectedness

High Sync 1502

GROUP SYNCHRONICITY:

We know that our stress response and emotional fitness are enhanced by a strong sense of connection. Lower frequency of heart rate synchronicity will exhibit minimal clarity – high scores will trend towards full clarity.

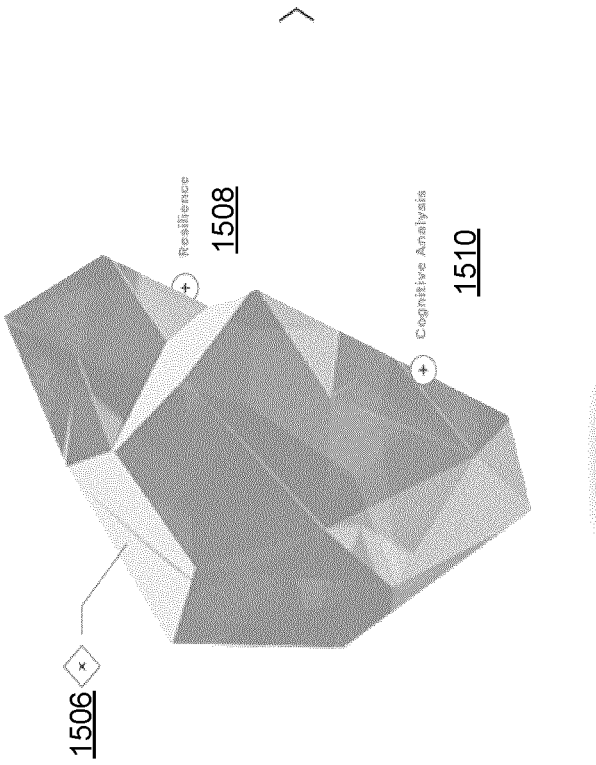

1504
1506
Resilience 1508
Cognitive Analysis 1510

SYNCHRONICITY BY POSE:

1512

GROUNDING  WARM-UP  HEAT-UP  STANDING  SEATED  FINALE

MY HISTORY

FIG. 15

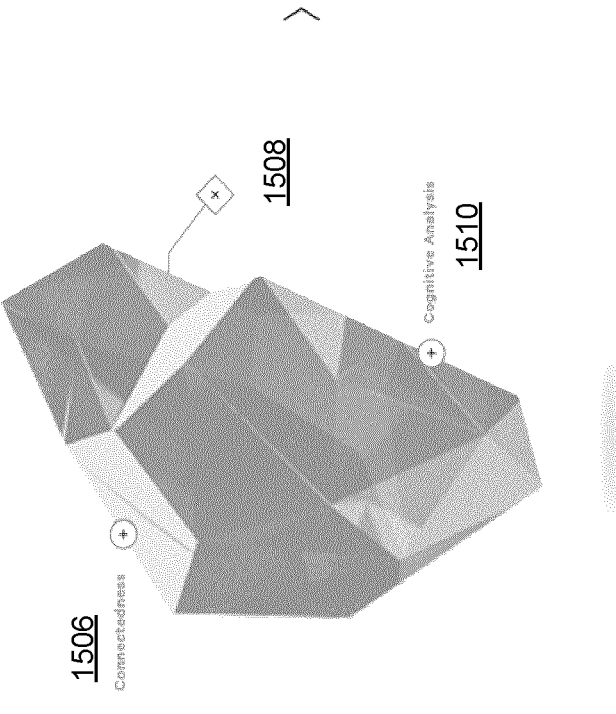
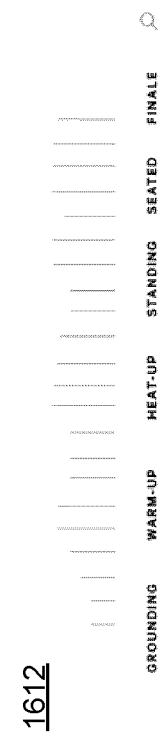
FIG. 16

TODAY, SEPTEMBER 26 / 45-MIN VINYASA

Cognitive Analysis

1700

1504

1506 Connectedness

1508 Resilience

1510 Cognitive Analysis

Positive 1702

INDIVIDUAL FEELING STATES:

Our meta-responses (rections to our emotional responses) ultimately determine our emotional fitness. Negative appraisals (higher stress levels) will generate an orange totem – positive appraisals (lower stress levels) will trend towards blue.

1712 COGNITIVE SHIFT

PRE-CLASS         POST-CLASS

MY HISTORY

FIG. 17

METHODS AND SYSTEMS FOR DETERMINING EMOTIONAL CONNECTIVITY USING PHYSIOLOGICAL MEASUREMENTS FROM CONNECTED DEVICES

CROSS REFERENCE TO RELATED APPLICATIONS

The application claims the benefit of and priority to U.S. Provisional Patent Application No. 62/936,203 filed Nov. 15, 2019 the contents of which is hereby incorporated herein by reference.

FIELD

This disclosure relates to methods and systems for determining an emotional fitness metrics and connectivity metrics of users for group activities using connected devices. In particular, the disclosure relates to methods and systems for capturing and processing physiological measurements from connected user devices during a group activity and comparing the measurements for a member of the group to metrics for other members of the group to compute emotional connectivity data and determine an emotional connectivity metric, a cognitive appraisal metric, a resilience metric and/or an emotional fitness metric.

BACKGROUND

Emotional health is intimately intertwined with physical health and, with the growing complexity of life, the relation between physiological conditions and emotional health has become of increasing interest. Many studies have shown that stress and other emotional factors may increase the risk of disease, reduce performance and productivity, and restrict quality of life. How a person handles stress or emotional factors may depend on the emotional intelligence or emotional fitness of each person.

Emotional intelligence refers to the capability of individuals to recognize their own emotions and those of others, discern between different feelings and label them appropriately, use emotional information to guide thinking and behavior, and manage and/or adjust emotions to adapt to environments or achieve goal(s). Emotional fitness is the ability of a person to maintain high emotional intelligence in the face of fatigue, overload or depletion. Emotional fitness is therefore an ability to demonstrate resilient emotional intelligence.

It has been previously shown that those with higher emotional intelligence experience higher life satisfaction and self-esteem, and lower levels of insecurity or depression. Those with higher emotional intelligence are also less likely to make poor health choices or behaviors.

Broadly speaking, there are three primary contributing factors to an individual's emotional fitness: 1. the stimuli and circumstances around the individual (environment), 2. the individual's physiological response to the environment (body), and 3. the individual's cognitive appraisal of both of these aspects (mind).

Physiological monitoring can be used in order to detect a person's emotional state by means of monitoring and analyzing the person's physiological response to their environment. For example, heart rate variability (HRV) can be used to derive health assessment metrics, such as overall health and wellness, fitness, and stress. Based on these physiological measurements, behavioral interventions can be suggested that then help people modulate their emotional health which in turn may affect their physical health.

Emotional health can also be improved by manipulating the environment of the individual and enhancing social support through group activities. For example, as choir singers perform, their heart rates can synchronize as they sing together. The structure of a song forces coordinated breathing between singers, which affects heart rate through respiratory sinus arrhythmia (Vickhoff, et al. (2013) *Front. Psychol*). Choir singing has also been associated with feelings of improved emotional health.

SUMMARY

In an aspect, the present disclosure is directed to methods and systems for using physiological measurements for a user during a group activity and comparing the measurements to those of other members of the group to determine an emotional connectivity metric, a cognitive appraisal metric, a resilience metric and/or an emotional fitness metric.

In an aspect, embodiments described herein relate to computer hardware systems for determining an emotional fitness metric for a group activity based on synchronicity of measured signals of physiological parameters of users acquired during a time period of the group activity. The system has non-transitory memory to receive and store measured signals of physiological parameters of users acquired during the time period of the group activity from a network. The system has a plurality of connected user devices for the group activity. Each user device has at least one biosensor to acquire a measured signal of a physiological parameter of a user during the time period of the group activity and having a transmitter to transmit the measured signal of the physiological parameters of the user acquired during the time period of the group activity over the network.

The system has one or more servers having a hardware processor coupled to the memory to access the measured signals of physiological parameters of the users acquired during the time period of the group activity to compute an emotional connectivity metric for the group activity. The hardware processor executes instructions stored in the memory to: identify measured signals of the physiological parameters of the users stored in the non-transitory memory using the group activity; time-synchronize the measured signals of the physiological parameters of the users; compute a normalized cross-correlation matrix with connectivity values for user pairings for the group activity corresponding to a synchronicity in a time-series correlation for the physiological parameters for permutations of the user pairings for the group activity by, for each user pairing of the permutations of user pairings for the group activity, comparing the time-synchronized measured signals for the physiological parameters of a user of the respective user pairing to the time-synchronized measured signals for the physiological parameters of another user of the respective user pairing. The hardware processor computes the emotional connectivity metric for the group activity using the normalized cross-correlation matrix with the connectivity values for the user pairings for the group activity corresponding to the synchronicity in the time-series correlation for the physiological parameters for the permutations of the user pairings for the group activity. The hardware processor transmits the emotional connectivity metric for the group activity to an interface at a computing device in communication with the one or more servers over the network for data exchange and programmed with executable instructions for generating visual elements representing the emotional connectivity metric for the group activity and at least a portion of the connectivity values for the user pairings for the group activity.

In some embodiments, the one or more servers use the connectivity values for the user pairings to identify a user pairing having a strong connectivity value for the group activity for the permutations of the user pairings for the group activity, wherein the interface visually indicates the user pairing having the strong connectivity value for the group activity.

In some embodiments, the one or more servers computes an overall group connectivity score for the group activity by calculating a group average of the connectivity values for the user pairings corresponding to the synchronicity in the time-series correlation for the physiological parameters for the permutations of the user pairings for the group activity, wherein the interface visually indicates the overall group connectivity score.

In some embodiments, the one or more servers clean and remove outliers from the measured signals of the physiological parameters of the users acquired during the time period of the group activity prior to the time-synchronize using an standard outlier filter to automatically remove any data points that are outside of a number of standard deviations from a group average.

In some embodiments, the one or more servers compute the connectivity values by computing a correlation score for each of the permutation of user pairings for the group activity and ranks the computed correlation scores to identify a user pairing having a strong connectivity value for the group activity for the permutations of the user pairings for the group activity, wherein the interface visually indicates the user pairing having the strong connectivity value for the group activity.

In some embodiments, the one or more servers control a user device of the plurality of connected user devices based on the computed emotional connectivity metric for the group activity.

In some embodiments, the one or more servers compute, based on the measured signals of the physiological parameters of the users, a variability of a physiological parameter of a user and determines a resilience metric based on such variability in the physiological parameter, receives inputs from a user device of an emotional state of the user before and after performing the group activity and determines a cognitive appraisal metric based on the two emotional state inputs, and determines an emotional fitness metric for the user according to:

Emotional Fitness Metric=Cognitive Appraisal(Emotional Connectivity Metric+Resilience Metric).

The server transmits over the network the emotional fitness metric for the user, the cognitive appraisal and/or the resilience metric to the interface at the computing device.

In some embodiments, the measured signals of the physiological parameters correspond to heart rate traces, wherein the physiological parameter is a heart rate and the at least one biosensor is a heart rate monitor. In some embodiments, the measured signals of the physiological parameters correspond to breathe rate traces, wherein the physiological parameter is a heart rate and the at least one biosensor is a breathe rate monitor. In some embodiments, the measured signals of the physiological parameters correspond to breath depth, and the at least one biosensor measures tidal volume.

In some embodiments, the one or more servers compute, based on the measured signals of the physiological parameters of the users, a variability of a physiological parameter of a user and determines a resilience metric for the user based on such variability in the physiological parameter, wherein the interface visually indicates the resilience metric for the user.

In some embodiments, the physiological parameter is a heart rate and the at least one biosensor is a heart rate monitor, wherein the variability of the physiological parameter is calculated by calculating a number of peaks and troughs in a heart rate curve.

In some embodiments, the calculating comprises counting and weighting the peaks and troughs in the heart rate curve.

In some embodiments, the physiological parameter is a breath rate.

In some embodiments, the one or more servers computes the emotional connectivity metric for the group activity based on correlation with an emotional fitness metric.

In some embodiments, the one or more servers generates a recommendation for a user of activities for improving the emotional fitness metric and wherein the interface visually indicates the recommendation.

In some embodiments, the one or more servers computes the emotional connectivity metric for the group activity after additional users have performed and completed the group activity and recorded their physiological parameter in a database, wherein the one or more servers compares the physiological parameter of the user with the physiological parameters recorded in the database.

In some embodiments, the users are performing the group activity at the same time. In some embodiments, the user and the one or more additional users are performing the group activity at the same time and in a same geographical location. In some embodiments, the user and the one or more additional users are performing the group activity at different times and/or at different geographical locations.

In some embodiments, the group activity comprises synchronicity of breath of the users. In some embodiments, the group activity is a yoga class.

In some embodiments, the one or more additional users are virtual users.

In some embodiments, the one or more servers computes the emotional connectivity metric for the group activity based on correlation with an emotional fitness metric.

In some embodiments, the system has one or more additional group devices in communication with the one or more servers over the network to receive control commands based on the emotional connectivity metric for the group activity during the time period for the group activity.

Various aspects of the present disclosure provide a method for determining an emotional fitness metric for a user, the method comprising: measuring a physiological parameter of the user during a group activity using at least one biosensor to acquire a measured signal, the group comprising the user and one or more additional users; comparing the measured signal for the physiological parameter of the user with measured signals for the physiological parameter of the one or more additional users as measured when the one or more additional users performed the group activity; and calculating an emotional connectivity metric based on a synchronicity of the physiological parameter of the user with the physiological parameter of the one or more additional users, the emotional connectivity metric being correlated with the emotional fitness metric of the user.

In various embodiments, the method further comprises measuring a variability of the physiological parameter of the user to determine a resilience metric; requesting inputs from the user of an emotional state of the user before and after performing the group activity and calculating a cognitive appraisal metric based on the two emotional state inputs; and calculating the emotional fitness metric of the user according to a formula: Emotional Fitness Metric=Cognitive Appraisal (Emotional Connectivity Metric+Resilience Metric).

Various aspects of the present disclosure also provide computer-readable media having stored thereon computer program code configured when executed by one or more processors to cause the one or more processors to perform a method as described herein.

Various aspects of the present disclosure also provide a system for determining an emotional fitness metric of a user, comprising: one or more servers storing measured signals for a physiological parameter during a group activity of one or more additional users; a network; a user device operable to communicate with the one or more servers over the network; and at least one biosensor operable to communicate with the user device, wherein the user device is configured to use the at least one biosensor to receive a measured signal of the physiological parameter of the user during the group activity, process the measured signal by comparing the measured signal for the physiological parameter of the user with the measured signals for the physiological parameter of the one or more additional users during the group activity and determining an emotional connectivity metric based on a synchronicity of the physiological parameter of the user with the physiological parameter of the one or more additional users, and transmit over the network the measured signal and emotional connectivity metric to the one or more servers.

In various embodiments, the user device further determines, based on the processed data, a resilience metric based on a variability of the physiological parameter of the user, receiving inputs from the user of an emotional state of the user before and after performing the group activity and determining a cognitive appraisal metric based on the two emotional state inputs, and determines the emotional fitness metric according to a formula: Emotional Fitness Metric=Cognitive Appraisal (Emotional Connectivity Metric+Resilience Metric); and transmits over the network the emotional fitness metric, the cognitive appraisal and/or the resilience metric.

Other aspects and features of the present invention will become apparent to those of ordinary skill in the art upon review of the following description of specific embodiments of the invention in conjunction with the accompanying claims.

BRIEF DESCRIPTION OF THE DRAWINGS

In drawings which illustrate embodiments of the disclosure,

FIG. 5A shows an example first set of values in a dataset containing measurements of heart rates of multiple users. FIG. 5B show the cross-correlation of the heart rate time series of users. FIG. 5C shows a ranked list of cross-correlation values for each combination of users in a group.

FIG. 7 shows the calculation of the resilience metric for a group of users.

FIG. 10 shows an example interface diagram for the system.

FIG. 11 shows another example interface diagram for the system.

FIG. 14 shows another example interface diagram for the system.

FIG. 15 shows another example interface diagram for the system.

FIG. 16 shows another example interface diagram for the system.

FIG. 17 shows another example interface diagram for the system.

DETAILED DESCRIPTION

Figure 1:
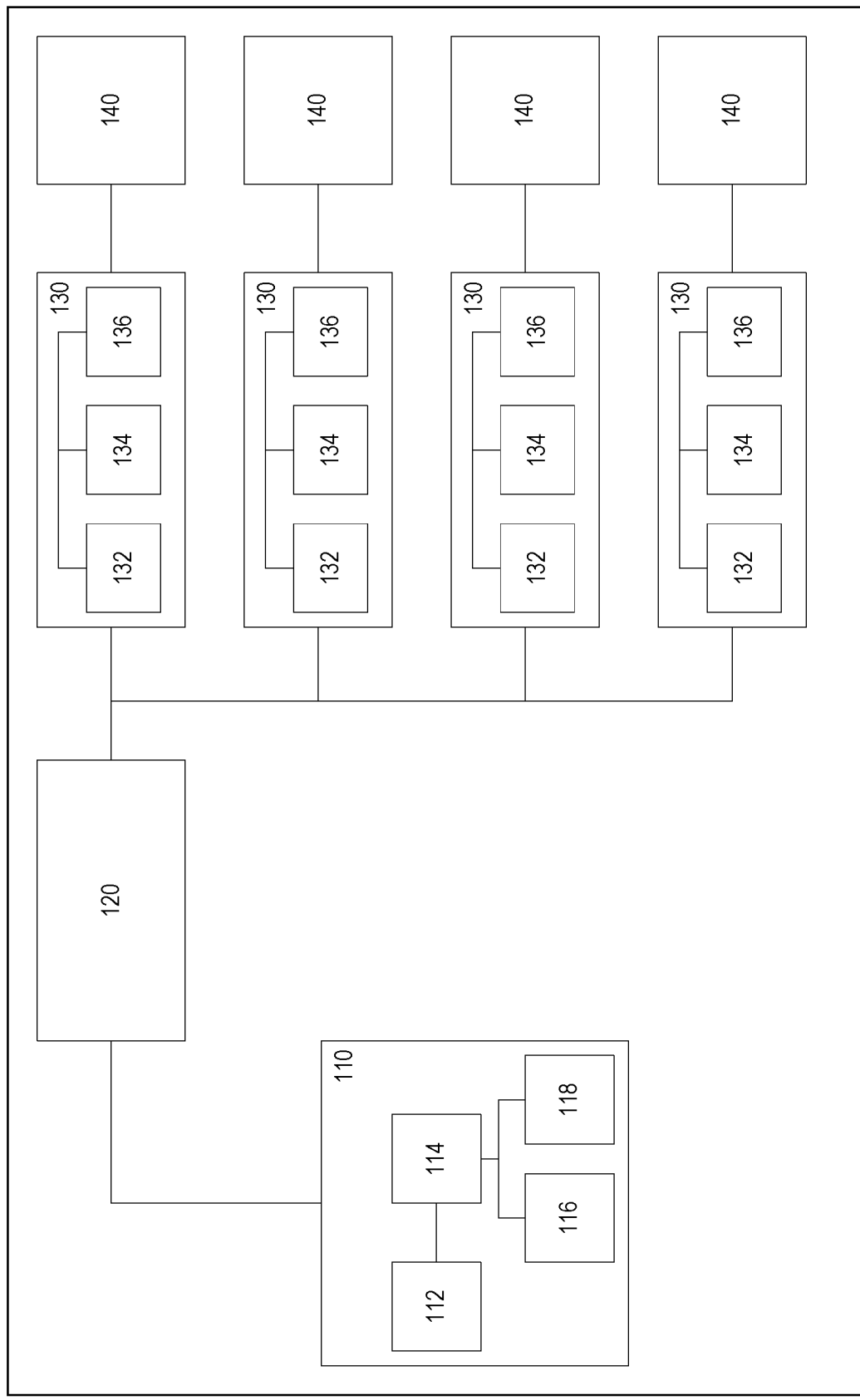
FIG. 1 is a system for measuring an emotional fitness metric of a user, in accordance with an embodiment of the invention.

In the context of the present disclosure, various terms are used in accordance with what is understood to be the ordinary meaning of those terms.

Systems and methods described herein can measure and quantify components of emotional health and emotional fitness using connected devices and improved computations for estimating metrics using computer systems. Methods and systems for determining an emotional fitness metric of a user for improving feelings of wellness and enhanced emotional health can be implemented using different hardware devices and system architectures.

Disclosed embodiments include systems, methods and non-transitory storage media associated with determining an emotional fitness metric for a user, based on both physiological measurements of the user during a group activity as well as physiological measurements of one or more additional users who are performing or have performed the same group activity. In various embodiments, the one or more additional users may be one or more additional participants that are performing or having performed the group activity at the same time and the same geographical location, at different times and/or different geographical locations or can be one or more virtual additional users that have been pre-recorded and their virtual physiological measurements have been stored in a memory and/or database. In various embodiments, the disclosure provides methods for determining an emotional fitness metric for the user, an emotional connectivity metric for the user, a cognitive appraisal metric of the user based on emotional state responses from the user before and after the group activity, and/or a resilience metric for the user, based on a physiological parameter of the user during the group activity. In various embodiments, the emotional fitness metric may increase the connectivity the user feels when engaged in the group activity. For example, individuals often feel alone or isolated during a fitness class, such as a yoga class, which is inherently a situation with more limited social interaction, and may feel stigma about how they look during the class. Connectedness may be a way of overcoming these issues, allowing users to feel more connected, engaged and having a sense of belonging during the group activity that then translates into a greater sense of belonging in their community and life outside of the group activity.

Emotional health can also be improved by manipulating the environment of the individual, for example, by actuating physical components, transmitting control commands to trigger programmatic response in computing devices, and enhancing social support through group activities.

An emotional fitness metric refers to a relative measure of an individual's resilient emotional intelligence, or how the individual perceives challenges in an environment and the support network that the individual builds through others. Resilient emotional intelligence refers to the individual's ability to adapt to stressful situations or crises. More resilient individuals adapt to adversity without lasting difficulties while less resilient individuals have a harder time with stress and life changes, both major and minor. Thus, in various embodiments, the emotional fitness metric may comprise at least three components: 1. environmental conditions (for example, an individual's support network of other people), 2. physical stress response to stimulus, and 3. cognitive appraisal of the response to stimulus.

Resilient emotional intelligence may be improved through a support network of other individuals. Such social and behavioural synchronicity has important evolutionary significance. The term "synchronicity" refers to a physiological event happening, existing or arising at approximately the same level. When a group of individuals are in physical synchronicity, as evidenced by, for example, common breathing or heart rate, they may achieve better social communication and connection, thereby improving resilient emotional intelligence. For example, heart rates of individuals may synchronize through collective rituals. A Spanish fire-walking ritual has been shown to induce similar heart rates in both active participants and related spectators (Konvalinka, et al. (2011) *PNAS* 108(20): 8514-8519). It has also been shown that romantic partners have similar heart rate and breathing patterns, without speaking or touching (Helm, et al. (2012) *Emotion* 12(4): 748-762).

Referring to FIG. 1 and according to an embodiment of the invention, a system for implementing the methods described herein is shown. The system 100 comprises a server 110, a network 120, user devices 130 and at least one biosensor 140. In some embodiments, the server 110 is communicatively coupled to a non-transient memory storing a database 116 and is operable to access data stored on database 116. The server 110 includes at least one hardware processor 112 and non-transient memory 114. The non-transient memory 114 stores a database 116 of records corresponding to received measured signals of physiological parameters of users and software programs 118. The server 110 is communicatively coupled to user devices 130 via network 120 (such as the Internet). Each user device 130 includes at least one hardware processor 132, non-transient memory 134 and an interface 136 that can display information and also communicate with the server 110 to exchange data. The interface 136 can also receive input data from users on feeling states before, during, or after the group activity. At least one biosensor 140 is communicatively coupled to each user device 130. In some embodiments, the biosensor 140 is integrated within the user device 130. In some embodiments, a biosensor 140 can communicate with multiple user devices 130. A user and one or more additional users may interface with user devices 130 in manners described below.

While system 100 is shown with one server 110 system 100 extends to any suitable number of servers 110 and databases 116. In various embodiments, the function of database 116 may be incorporated with that of server 110. In other words, server 110 may store the data located on database 116 and may additionally perform any of the processing of data described in further detail below. The function of at least one biosensor 140 may also be incorporated with that of user device 130.

The system 100 can be integrated with a sensory environment with controls for sensory actuators to create a multi-sensory ecosystem for a group activity. An example group activity is a yoga class and the system 100 can control a sensory environment for the yoga class that is driven by the computations of server 110 on the collected measured signals of physiological parameters of users, for example. The server 110 can compute tangible metrics associated with fluidity and synchronicity that can be displayed at user device 130 (and interface 136) as feedback and visual elements for computed metrics. The feedback can be in real-time and post-class or activity for reflection or comparison with self and others of the group. The display of visual elements at interface 136 can be driven by the server 110 computing metrics from measured signals of physiological parameters collected from user devices 130 and sensors 140.

The system 100 has computer hardware components for determining an emotional fitness metric for a group activity based on synchronicity of measured signals of physiological parameters of users acquired during a time period of the group activity. The system 100 has non-transitory memory 114 to receive and store measured signals of physiological parameters of users acquired during the time period of the group activity from a network 120. The system 100 has a plurality of connected user devices 130 for the group activity. Each user device 130 has at least one biosensor 140 to acquire a measured signal of a physiological parameter of a user during the time period of the group activity and has a transmitter to transmit the measured signal of the physiological parameters of the user acquired during the time period of the group activity over the network 120.

In some embodiments, the measured signals of the physiological parameters correspond to heart rate traces, the physiological parameter is a heart rate and the at least one biosensor is a heart rate monitor. In some embodiments, the physiological parameter is a breath rate. Other example measured signals and physiological parameters of users relate to breathe depth or tidal volume. Further example measured signals and physiological parameters of users relate to heart rate variability. The physiological parameters of a user can have relations to other physiological parameters of the user. For example, there can be a relationship between breathe depth or tidal volume and heart rate variability. An example relationship between these variables can be that breathing is the combination of how many times you breath per time period (e.g. minute), which can also be referred to as breathing rate, multiplied by the amount of air you breath in and out in each breath cycle (tidal volume, also referred to as breathing depth). The physiological parameters can be used as input variables for the system to compute synchronicity and connection metrics. There can be heart rate synchronicity for the connection metrics or breathing rate synchronicity for the connection metrics. The breathing depth can inform the resilience metric similar to how heart rate can be used for a measure of hard someone is working.

The system 100 has one or more servers 110 having a hardware processor 112 coupled to the memory 114 to access the measured signals of physiological parameters of the users acquired during the time period of the group activity to compute an emotional connectivity metric for the group activity. The hardware processor 112 executes instructions stored in the memory 114 to identify measured signals of the physiological parameters of the users stored in the non-transitory memory 114 using the group activity. The measured signals can be stored as records indexed by a group activity identifier, for example. The hardware processor 112 can identify the records using the group activity identifier to identify a group of users for the activity. The hardware processor 112 can access data in the records to compare physiological parameters of a user to other physiological parameters of the user. In some embodiments, the hardware processor 112 can access data in the records to compare multiple physiological parameters of a user and be compared to physiological parameters of another user.

The hardware processor 112 time-synchronizes the measured signals of the physiological parameters of the users. The signals can be associated with different time stamps that can be read by the processor 112, for example. For example, the measured signals of the physiological parameters can correspond to heart rate traces, breath rate, breath depth, and so on. For example, the hardware processor 112 time-synchronizes the heart rate traces for the group activity for the time period. The group activity can have a corresponding time period and the hardware processor 112 time-synchronizes the heart rate traces.

In some embodiments, the hardware processor 112 computes a normalized cross-correlation matrix with connectivity values for user pairings for the group activity corresponding to a synchronicity in a time-series correlation for the physiological parameters for permutations of the user pairings for the group activity. The group activity can involve a set of users that can be paired into different permutations of user pairings. The set of users can be user 1, user 2, user 3, user 4, user 5, user 6, for example. Different permutations of user pairings can be (u1, u2), (u1, u3), (u1, u4), (u1, u5), (u1, u6), (u2, u3), (u2, u4), (u2, u5) . . . and so on. The hardware processor 112 can identify a set of users for the group activity using different identifiers for the group activity, including a unique group activity identifier, activity type, location data, time data, and so on. The hardware processor 112 can compute different permutations of user pairings for the set of users for the group activity. The different permutations of user pairings can be used for comparing measured signals and physiological parameters of users of the same user pairing to compute connectivity values, for example. The different permutations of user pairings can also be referred to as combinations of participants of the group activity.

For each user pairing of the permutations of user pairings for the group activity, the hardware processor 112 compares the time-synchronized measured signals for the physiological parameters of a user of the respective user pairing to the time-synchronized measured signals for the physiological parameters of another user of the respective user pairing. For an example user pairing (user 1, user 2), the hardware processor 112 compares the time-synchronized measured signals for the physiological parameters of user 1 to the time-synchronized measured signals for the physiological parameters of user 2 to compute connectivity values for the user pairing (user 1, user 2).

The normalized cross-correlation matrix can have connectivity values for all permutations of user pairings for the group activity. The connectivity values can provide estimations for synchronicity in a time-series correlation for the physiological parameters for permutations of the user pairings for the group activity.

The hardware processor 112 computes the emotional connectivity metric for the group activity using the normalized cross-correlation matrix with the connectivity values for the user pairings for the group activity. The hardware processor 112 computes the emotional connectivity metric corresponding to the synchronicity in the time-series correlation for the physiological parameters for the permutations of the user pairings for the group activity.

The hardware processor 112 transmits the emotional connectivity metric for the group activity to an interface 136 at a user device 130 in communication with the one or more servers 110 over the network 120 for data exchange. The user device 130 is programmed with executable instructions for generating the interface 136 with visual elements representing the emotional connectivity metric for the group activity and at least a portion of the connectivity values for the user pairings for the group activity. The interface 136 provides improved visualizations corresponding to the emotional connectivity metrics. The display of raw data for the processed signals might not visually indicate estimations of connectivity between users of a group activity. The improved interface 136 provides improved visualizations to indicate estimations of connectivity between users of a group activity.

In some embodiments, the one or more servers 110 use the connectivity values for the user pairings to identify a user pairing having a strong connectivity value for the group activity for the permutations of the user pairings for the group activity. The interface 136 can receive control commands and data to visually indicate the user pairing having the strong connectivity value for the group activity.

In some embodiments, the one or more servers 110 computes an overall group connectivity score for the group activity by calculating a group average of the connectivity values for the user pairings corresponding to the synchronicity in the time-series correlation for the physiological parameters for the permutations of the user pairings for the group activity. The interface 136 can receive control commands and data to visually indicate the overall group connectivity score.

In some embodiments, the one or more servers 110 clean and remove outliers from the measured signals of the physiological parameters of the users acquired during the time period of the group activity prior to the time-synchronize using an standard outlier filter to automatically remove any data points that are outside of a number of standard deviations from a group average.

In some embodiments, the one or more servers 110 compute the connectivity values by computing a correlation score for each of the permutation of user pairings for the group activity. The one or more servers 110 rank the computed correlation scores to identify a user pairing having a strong connectivity value for the group activity for the permutations of the user pairings for the group activity. The interface 136 can receive control commands and data to visually indicate the user pairing having the strong connectivity value for the group activity.

In some embodiments, the one or more servers 110 control a user device 130 of the user devices 130 based on the computed emotional connectivity metric for the group activity.

In some embodiments, the one or more servers 110 compute, based on the measured signals of the physiological parameters of the users, a variability of a physiological parameter of a user and determines a resilience metric based on such variability in the physiological parameter. The server 110 can receive inputs from a user device 130 of an emotional state of the user before and after performing the group activity and determines a cognitive appraisal metric based on the two emotional state inputs, and determines an emotional fitness metric for the user according to:

Emotional Fitness Metric=Cognitive Appraisal(Emotional Connectivity Metric+Resilience Metric).

The server 110 transmits over the network the emotional fitness metric for the user, the cognitive appraisal and/or the resilience metric to the interface at the computing device.

In some embodiments, the one or more servers 110 compute, based on the measured signals of the physiological parameters of the users, a variability of a physiological parameter of a user and determine a resilience metric for the user based on such variability in the physiological parameter. The interface 136 can visually indicate the resilience metric for the user. In some embodiments, the physiological parameter is a heart rate and the at least one biosensor is a heart rate monitor. The server 110 can compute the variability of the physiological parameter by calculating a number of peaks and troughs in a heart rate curve. In some embodiments, the calculating comprises counting and weighting the peaks and troughs in the heart rate curve.

In some embodiments, the physiological parameters correspond to heart rate, breath rate, breathe depth or tidal volume. The physiological parameters of a user can have relations to other physiological parameters of the user. For example, there can be a relationship between breathe depth or tidal volume and heart rate variability. An example relationship between these variables can be that breathing is the combination of how many times you breath per time period (e.g. minute), which can also be referred to as breathing rate, multiplied by the amount of air you breath in and out in each breath cycle (tidal volume).

The physiological parameters can be used as input variables for the server 110 to compute synchronicity and connection metrics. There can be heart rate synchronicity for the connection metrics or breathing rate synchronicity for the connection metrics.

The breathing depth can inform the resilience metric similar to how heart rate can be used for a measure of hard someone is working.

Heart rate variability (HRV) can be see in real time as being affected by changing or synchronizing someone's breathing to a specific rhythm. For example, the system can use multi-sensory signals (lights, sound, content) to prescribe a specific breathing rate, and then the system can use HRV as a metric of how well someone is able to use that breathing tool to calm themselves down. The system can have a content creation system to help prescribe breath rate.

In some embodiments, the one or more servers 110 computes the emotional connectivity metric for the group activity based on correlation with an emotional fitness metric.

In some embodiments, the one or more servers 110 generates a recommendation for a user of activities for improving the emotional fitness metric. The interface 136 visually indicates the recommendation.

In some embodiments, the one or more servers 110 compute the emotional connectivity metric for the group activity after additional users have performed and completed the group activity and recorded their physiological parameter in a database 116. The one or more servers 110 compare the physiological parameter of the user with the physiological parameters recorded in the database 116.

In some embodiments, the users are performing the group activity at the same time. In some embodiments, the user and the one or more additional users are performing the group activity at the same time and in a same geographical location. In some embodiments, the user and the one or more additional users are performing the group activity at different times and/or at different geographical locations.

In some embodiments, the group activity comprises synchronicity of breath of the users. In some embodiments, the group activity is a yoga class. In some embodiments, the one or more additional users are virtual users.

In some embodiments, the one or more servers computes the emotional connectivity metric for the group activity based on correlation with an emotional fitness metric.

In some embodiments, the system 100 has one or more additional group devices in communication with the one or more servers 110 over the network to receive control commands based on the emotional connectivity metric for the group activity during the time period for the group activity.

Figure 2:
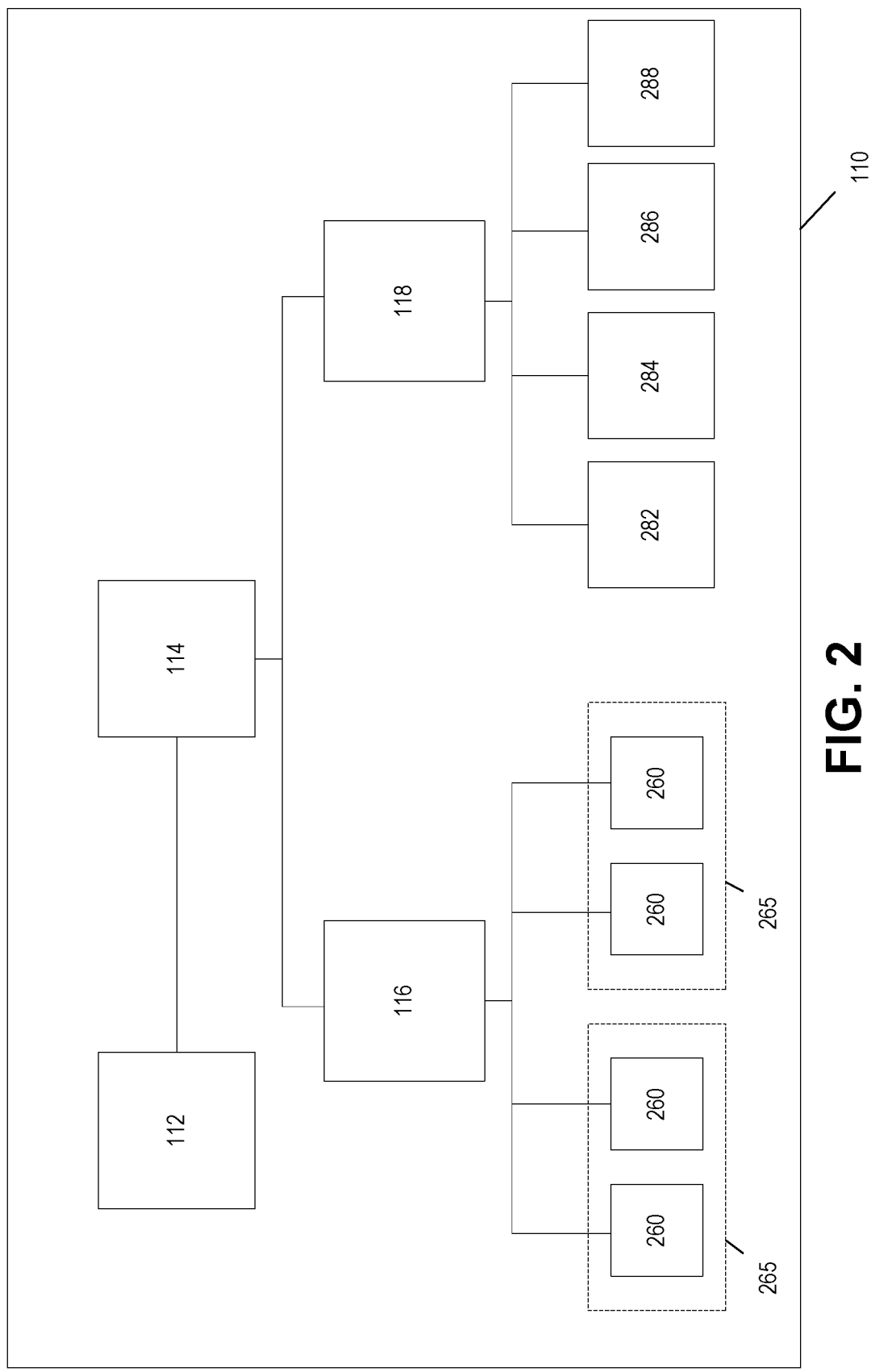
FIG. 2 shows a server, in accordance with one aspect of an embodiment of the invention.

Referring to FIG. 2 and according to an aspect of an embodiment described herein, a server 110 is shown. The server 110 includes at least one hardware processor 112 and non-transient memory 114. The non-transient memory stores a database 116 and software programs 118. The database 116 contains records 260 corresponding to received measured signals of physiological parameters of users. The records 260 can be in groups 265 corresponding to sets of related records for users of the group activity.

The server 110 can acquire measured signals for computing physiological measurements for a group activity. The server 110 can identify a group 265 of records 260 as user data of the group activity. The server 110 can process acquired measured signals of the group 265 of records 260 to compute cognitive metrics.

For example, the server 110 can identify a group 265 by location and time, and the server 110 can generate and assign a unique identifier for the group 265 to tag the group 265 of records 260 together. As an illustrative example, a unique identifier (uuid) for the group 265 can be a universally unique string of numbers and letters [ex: BE7BAF82-66DA-4021-8153-942E5BFDAADA] to tag the records 260. The records 260 can be associated with different users or measured signals from different users acquired during the group activity. The records 260 can map to different user pairings for the group activity.

In some embodiments, the groups 265 can be dynamically defined based on different group parameters that map to data values of the records 260. An example can be a proximity or location group parameter that defines a group 265 based on location data in records 260 and in particular records 260 that have proximate location data to define a group of records 260. The data in records 260 can be near real-time data for example and the groups 265 can be defined dynamically based on the mapping between the near real-time data and the group parameters. The groups 265 can update over time based on the records 265, for example. The group parameters can be used to identify a set of records 260 for a group 265. The set of records 260 can correspond to measured signals or parameters of users of the group activity acquired by the connected user devices 130 and sensors 140.

The software programs 118 include software for identifying measured signals stored in the database 282, software for comparing the measured signals for different permutations of user pairings stored in (or that map to) records 260 of the same group 265 in the database 284, software for computing a normalized cross-correlation matrix to reflect a synchronicity in the signals in a particular group in the database 286, and software for computing an emotional connectivity metric based the synchronicity 288.

For example, the server 110 can define a group 265 of records 260 based on data received from the user device 130. The group activity can occur in a room that may have a near field communication (NFC) tag outside the door, a QR code, or a unique number. When an individual enters the room they swipe their user device 130 near the tag, or enter the code. In the backend, the server 110 tags records 260 for the individuals by the near time stamp for the group 265.

As another example, the server 110 can define a group 265 of records 260 based on proximity and time. The user device 130 includes at least one hardware processor 132 that executes an application stored in non-transient memory 134 to provide an interface 136 that can display information and also communicate with the server 110 to exchange data. The user device 130 application can detect applications on other user devices 130 nearby using communication protocols, such as Bluetooth. The server 110 can identify records 260 corresponding to those devices 130 as a group 265.

The server 110 can also receive group data from electronic messages or notifications inviting users to attend a group activity.

The server 110 can use different parameters to classify different groups 265 and events. For example, the server 110 can detect a number of connected sensors 140 (e.g. heart rate monitors) via user devices 130, and each session dataset is tag with a date stamp and group identifier.

The group 265 of records 260 can correspond to devices 130 in physical proximity or the devices 130 can be connected as a virtual group. The server 110 can overlay curves and data to get metrics for physically grouped users or virtually grouped users.

A user be linked to multiple devices 130 or sensors 140 to acquire different types of signals/physiological parameter. The server 110 can manage these different types of signals for a user and physiological parameters for the user on the backend by linking the data in records 260 indicating a user identifier. The user identifier can be associated with a group identifier for one or more group activities. The different types of signals and physiological parameters can map to different input variables into functions for computing cognitive metrics and weighting the data.

The server 110 can process the signals to extract accurate measurements. The server 100 can execute code for a standard outlier filter to automatically remove any data points that are outside of a number of standard deviations from the group average at any time point. An example is a standard outlier filter to automatically remove any data points that are outside two standard deviations from the group average at any time point.

The server 110 can compare the measured signal for the physiological parameter of the user with the measured signals for the physiological parameter of other users during the group activity to consider permutations of different user pairings. The system 100 can manage comparison of multiple physiological parameters for a user against multiple physiological parameters of other users by having multiple dimensions of connectivity values for different user pairings.

The server 110 can combine the parameters into metrics corresponding to an individual or user of the group. The server 110 can then compare metrics between individuals of the group. For example, the server 110 can compare two within-subject parameters for users by considering the lag time between the parameters based on the cross-correlation of the time-series data in order to surface parameters that are too fast or too slow to give the server 110 feedback about parameters to adjust.

The server 110 can compute an emotional connectivity metric based on synchronicity of the physiological parameters of the users. Examples of physiological events can relate to heart rate synchronicity or breathe rate synchronicity with movement data, for example.

The server 110 can time-synchronize signals for all users for an event of the group activity to compute cognitive and physical metrics for the users or participants of the group activity.

The server 110 can compute cross-correlation of time-series traces to time-synchronize signals. The server 110 can use different acceptability thresholds for the time-series traces. The acceptability thresholds can correspond to particular users based on previous data received by server 110 in relation to the user, for example.

The server 110 can compute different synchronicity values between users for overall group computations. The server 110 can compute cross-correlation of all time-series data for users for overall group computations.

The server 110 can compute connectivity metrics regarding group connectivity or individual connectivity programmatically with the sensor 140 input data for different permutations of user pairings or combinations of participants of the group activity. The sensory data can be used by the server 110 to compute connectivity metrics for a group activity to indicate how connected one person is to anyone else in the group, or how connected one person is to the entire group. The server 110 can compute a numeric value to estimate "togetherness" of a group. This can manifest itself visually at the interface 136 with visual elements corresponding to connectivity metrics for the group 165. For example, the interface 136 can have visual elements with a color shift in the graphics shown to the group 165. The interface 136 can also depict a number or visual indication shown after a group activity. The connectivity metrics provide correlation values for how close each user's heart rate trace was at each moment in time during the group activity. Instead of measuring the heart rate value alone, the server 110 can measure how heart rate values for users of a group compare to everyone else's values during that time of the group activity at the same time, and whether by the same amount (as a proxy for connected moving/breathing). In an example, the closer the connectivity metric is to 100, the more connected everyone in the group is.

Figure 3:
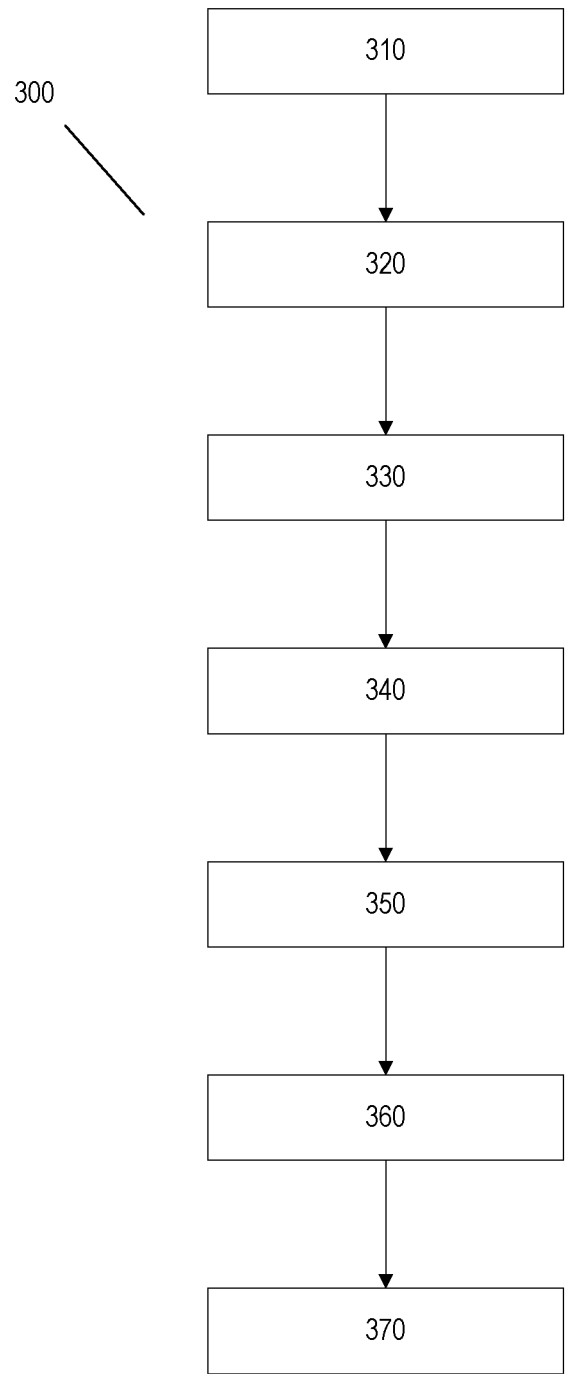
FIG. 3 is a block diagram of a method for determining an emotional fitness metric for a user, in accordance with an embodiment of the invention.

Referring to FIG. 3 and according to an embodiment of the invention, a method 300 for determining an emotional fitness metric for a user is shown. The method 300 can be implemented by server 110. The method shown generally in FIG. 3 is a flow diagram of the steps that may be taken to generate the emotional fitness metric for the user by the server 110. As the skilled person would recognize, the steps shown in FIG. 3 are exemplary in nature, and the order of the steps may be changed, and steps may be omitted and/or added without departing from the scope of the disclosure.

The server 110 can compute emotional fitness metrics and physical fitness metrics. The server 110 can compute emotional fitness metrics by defining rules for computing approximate values for environmental conditions, physical stress response to stimulus (body), and cognitive appraisal of the response (mind). The hardware processor 112 transmits the emotional fitness metrics to an interface 136 at a user device 130 in communication with the one or more servers 110 over the network 120 for data exchange. The user device 130 is programmed with executable instructions for generating the interface 136 with visual elements representing the emotional fitness metrics for the group activity. The interface 136 provides improved visualizations corresponding to the emotional fitness metrics. The improved interface 136 provides improved visualizations to indicate estimations of emotional fitness for users of the group activity.

The server 110 can compute emotional fitness metrics over a time period for the group activity. The server 110 can compute different emotional fitness metrics over a time period for the group activity. The computed emotional fitness metrics over the time period for the group activity can indicate accumulation and progression of emotional fitness throughout the group activity. The server 110 can compute emotional fitness metrics by defining rules for computing approximate values for cognitive metrics for an appraisal of and reaction to environmental conditions and a response to triggers of the environmental conditions.

The method 300 comprises measuring a physiological parameter of the user during a group activity at a number of time intervals using at least one biosensor 310 to acquire at least one measured signal 320 for the group activity. The measurements may be taken once every minute, once every 30 seconds, once every 15 seconds, once every second, or any time there between based on sampling configurations that can be defined at device 260 or biosensors 230. In some embodiments, at least one of the at least one biosensors 230 may be used to acquire two or more measured signals 320.

The physiological condition may be measured using at least one biosensor 310 as would be known to a person of ordinary skill in the art. For example, there are several smartphone, smartwatch and apps that offer measurement of a physiological parameter. The physiological parameter may be breathing rate or breathing depth. The physiological parameter may be heart rate and the at least one biosensor may be a heart rate monitor.

The method 300 further comprises transferring the measured signals to a processing unit, such as, for example, a microprocessor operatively connected to the at least one biosensor. The processing unit may be any of various microprocessors as will be recognized by those of ordinary skill in the art. The processing unit is configured to receive data signals from the at least one biosensor, and process such signals, as described below. The processing unit may be part of a user device, such as a smartphone, smartwatch, or laptop. The at least one biosensor may be incorporated into the same device or a separate device.

The group activity may be a fitness class, such as, for example, a yoga class. The group activity may also be a running or walking route that is completed by the user and one or more additional users at the same time or at different times. The group activity may be performed by the user and one or more additional users at the same time but at different geographical locations or at different times and the same or different geographical locations. The user and additional users correspond to different permutations of user pairings for the group activity. The measured signal for the user and each of the one or more additional users is transferred separately to the processing unit and the processed signal is stored in a memory and/or database.

In various embodiments, where the at least one biosensor is separate from the processing unit, the processing unit may use SPI to send data between the at least one biosensor and the processing unit. For example, the at least one biosensor may be connected to a heart rate strap via Bluetooth Smart or other type of heart rate sensor. The heart rate sensor may be a smart heart rate device configured to communicate using Wi-Fi, Bluetooth®, and/or a cellular network protocol to transmit measurements to a secure database or directly to another electronic device incorporating the processing unit, such as a smart watch, a smart tablet, or a phone.

In these embodiments, the at least one biosensor may comprise a transceiver, such as an RF transmitter and receiver, configured to transmit and receive communications signals over a short range using wireless communications technology, such as Bluetooth®, using any of various communications protocols.

The transmission of data from the at least one biosensor to the processing unit may occur automatically without the user needing to prompt the transmission. For example, some mechanism may be used to turn on the at least one biosensor or otherwise indicate that automatic transmissions should begin. In other embodiments, the transceiver may be configured to begin transmissions once it receives a confirmation from the display device or when the display device is within an appropriate range of the transceiver. In other embodiments, data transmission may occur periodically at predetermined intervals of time.

Raw data collected by the at least one biosensor may be processed by the processing unit and/or delivered to a remote server for processing. Typical processing may include associating each measurement with a time stamp, associating each membership with a group comprising the one or more additional users, and comparing the measured signal for the user with the measured signal for the physiological parameter of the one or more additional users as measured when the one or more additional users performed or are performing the group activity, as described below. Furthermore, the physiological condition data may be processed into different forms and formats, depending on the particular device that will be ultimately used to view the data.

The processing unit may be connected to a memory and/or database, and may deliver processed data to the memory and/or database. Additionally, the processing unit may perform processing of the received data prior to delivery thereof to the memory and/or database.

A comparison of the measured signal of the user with a measured signal for the physiological parameter of one or more additional users within the same group is used to calculate an emotional connectivity metric. Different permutations of user pairings (or dyads) can define comparison rules for the measured signals and parameters. A user may be associated with at least one group, consisting of at least two users. Users may be associated with a group through a variety of methods. For example, users may be manually added to a group by accepting an invitation to join the group sent via email, by entering a group identification number on a user device, by scanning a QR code on a user device, or via NFC tags. User may also be added to a group automatically, for example via a software application that uses Bluetooth communications between at least two user devices to associate users who are using the application in physical proximity to one another with a group.

A measured signal may be associated with at least one group activity, performed by members or users of a group. The members of the group may perform the group activity at the same time or at different times. Signals may be associated with a group activity. For example, a yoga instructor interface may create a group activity to represent a yoga class via a software application and add class participants to the group activity via the software application, thereby associating their corresponding measured signals to the group activity. The server 110 can associate user signals with an activity automatically (e.g. recognizing there are multiple user devices close together and engaging in a physical activity at the same time. The participants in the group activity can provide different permutations of user pairings for computing connectivity metrics for the group activity.

A comparison of the measured signal of the user with a measured signal for the physiological parameter of one or more additional users as measured when the one or more additional users are performing the group activity at the same time as the user or perform the group activity either before or after the user is used to calculate an emotional connectivity metric based on a synchronicity of the measured signal for the physiological parameter of the user and the one or more additional users, the emotional connectivity metric being correlated with the emotional fitness metric of the user (30).

Figure 4B:
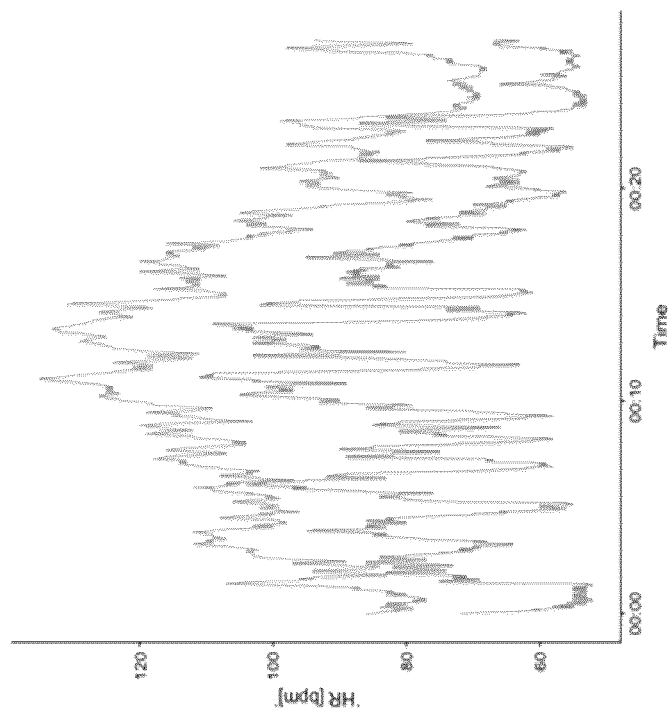
FIG. 4A shows heart rate traces of two users with higher heart rate synchronicity and FIG. 4B shows heart rate traces of two users with lower heart rate synchronicity.
Figure 4A:
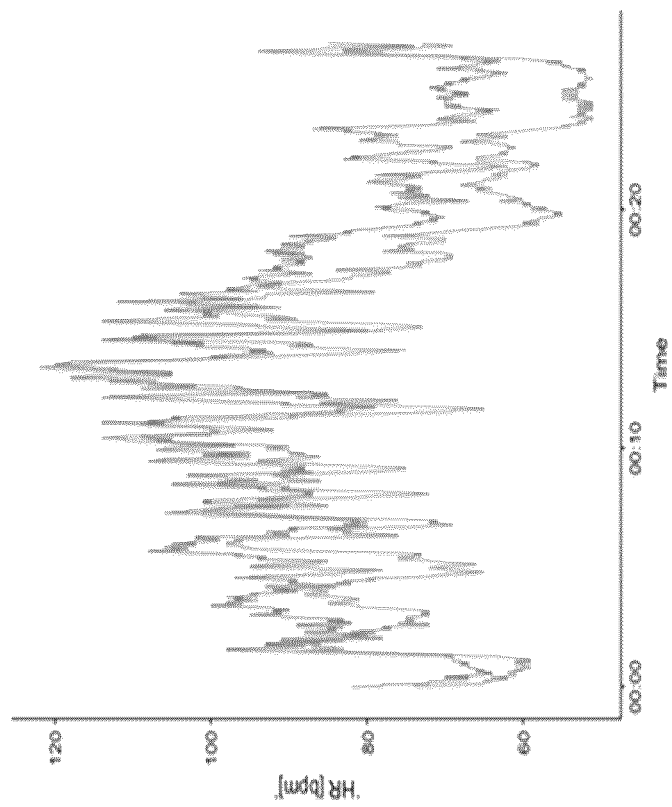

The server 110 can compute a 'connection metric' or connectivity value that can be used for computation of the emotional connectivity metrics. Given that an individual's stress response, and therefore emotional fitness, is enhanced by connection and strong support networks, this connection metric may be represented by server 110 using different functions that provide values for the emotional connectivity metric which shows how the bodies of the user and the one or more additional users are in synchronicity. The higher the synchronicity, the more connected the user may feel to the one or more additional users that are participating in the group activity. An example of heart rate traces for two users with higher heart rate synchronicity is shown in FIG. 4A, while heart rate traces for two users with lower heart rate synchronicity is shown in FIG. 4B. The interface 136 can generate visualizations corresponding to the heart rate traces for two users such as the graph examples shown in FIGS. 4A, 4B.

For example, the synchronicity of the user's heart rate traces may be used as a measure for connection through a challenging physical group activity, such as, for example, a yoga class.

In order to allow comparison of the measured signal the user with the measured signal of one or more additional users, the measured signals can be filtered by the server 110 to remove any anomalous or outlier data points. This may be done, for example, by the server 110 removing any data points that are more than two standard deviations from the mean value of the measured signal.

For this example, the server 110 can collect heart rate traces as measured signal for the physiological parameter of one or more additional users using sensors 140 or device 130. The server 110 receives the heart rate traces as input data corresponding to beat-to-beat heart rate files. The server 110 can remove outliers and time-sync the heart rate data for all participants of the group activity. The server 110 can store the measured signals in records and/or store the processed signals that have been time-synced and filtered to remove outliers.

In various embodiments, the users may not begin measuring the physiological parameter at the same time. For example, one user may arrive to a yoga class and begin collecting data earlier than a second user, or some members of the group may be participating in the group activity earlier or later than other users. In order to allow the comparison of the measured signals, in embodiments where the user may not begin measuring the physiological parameter at the same time, one or more of the measured signals may undergo a phase shift by the server to synchronize the signals so that the signals each represent a time series, with the different time series corresponding to the values of the measured signal at the same point in time during the group activity or events of the group activity.

The server 110 can be configured with computer code to process the input data to compute a normalized cross-correlation matrix to reflect the synchronicity in time-series correlation for all permutations of user pairings or participant connections.

The following example code snippet can be used to compute a normalized cross-correlation matrix to reflect the synchronicity in time-series correlation for all permutations of user pairings or participant connections:

```
correlationTable = function (HRCorr1) {
cross=matrix(nrow = length(HRCorr1),ncol=length(HRCorr1))
for(P1ID in 1:length(HRCorr1)) {
subject1 = HRCorr1[[P1ID]]
print(P1ID)
for(P2ID in 1:length(HRCorr1)) {
subject2 = HRCorr1[[P2ID]]
if(P1ID == P2ID){
break;
} else {
correlation = ccf(subject1,subject2,lag.max=0,na.action=na.pass,plot=FALSE)
cross[P1ID,P2ID] = correlation$acf[1]
}
}
}
Cross
}
corr= as.data.frame(correlationTable(HRCorr1))
```

FIG. 5A shows sample input data for the server 110 that can be processed using the computer code to compute the normalized cross-correlation matrix to reflect the synchronicity in time-series correlation for all permutations of participant connections. The data shows a measured physiological parameter, beat-to-beat heart rate, for 8 individuals attending a yoga class as an example group activity.

FIG. 5B shows sample output data for server 110 that can be processed using the computer code. The result is a dataset of values approximating the cross-correlation of all of the permutations of user connections for users of the group activity. The server 110 identifies a group activity and a set of users for the group activity. The server 110 accesses non-transitory memory storing user data to compute values approximating the cross-correlation of all of the permutations of user connections for the set of users. The permutations correspond to different pairings of users of the set of users and the values correspond to different synchronicity computations based on user data corresponding to the pairings of users.

The following example code snippet can be used to sort data values from the normalized cross-correlation matrix that reflects the synchronicity in time-series correlation for all permutations of participant connections. The server 110 can process the data from the normalized cross-correlation matrix into a list of participant dyads (user pairings) sorted by the strongest correlation scores. The output of the server 110 can indicate user pairings that were most connected during the group activity based on synchronicity computations.

```
Corr1 <- corr %>%
gather(Participant2, HR_Synchronicity1,-Participant1) %>%
filter(!is.na(HR_Synchronicity1)) %>%
mutate(HR_Synchronicity=as.numeric(HR_Synchronicity1)) %>%
select(-HR_Synchronicity1) %>%
filter(!is.na(HR_Synchronicity)) %>%
mutate(HR_Synchronicity=round(HR_Synchronicity,3)) %>%
arrange(desc(HR_Synchronicity))
Inverse <- Corr1 %>%
mutate(Participant4=Participant2,Participant3=Participant1) %>%
select(Participant4,Participant3,HR_Synchronicity)
colnames(Inverse) <- c("Participant","Participant2","HR_Synchronicity")
Corr2 <- rbind(Corr1,Inverse)
```

FIG. 5C shows the data from the table in FIG. 5B, rearranged into a table with each row representing a different user pairings or dyads. The table is sorted by cross-correlation in order to determine which pairings had the highest and lowest synchronicity as an example.

The server 110 can compute data values corresponding to group correlations to provide an estimated value for an overall group connectedness metric. The following example code snippet can be used by server 110 to calculate group average of correlations to provide an estimated value for an overall group connectedness metric.

```
OverallSync <- Corr2 %>%
group_by(Participant1) %>%
summarize(MeanSync = mean(HR_Synchronicity),SDSync=sd(HR_Synchronicity)) %>%
mutate(MeanSync=round(MeanSync,3),SDSync=round(SDSync,3)) %>%
arrange(desc(MeanSync)) %>%
mutate(MeanSync=MeanSync*100,SDSync=SDSync*100)
```

Figure 6:
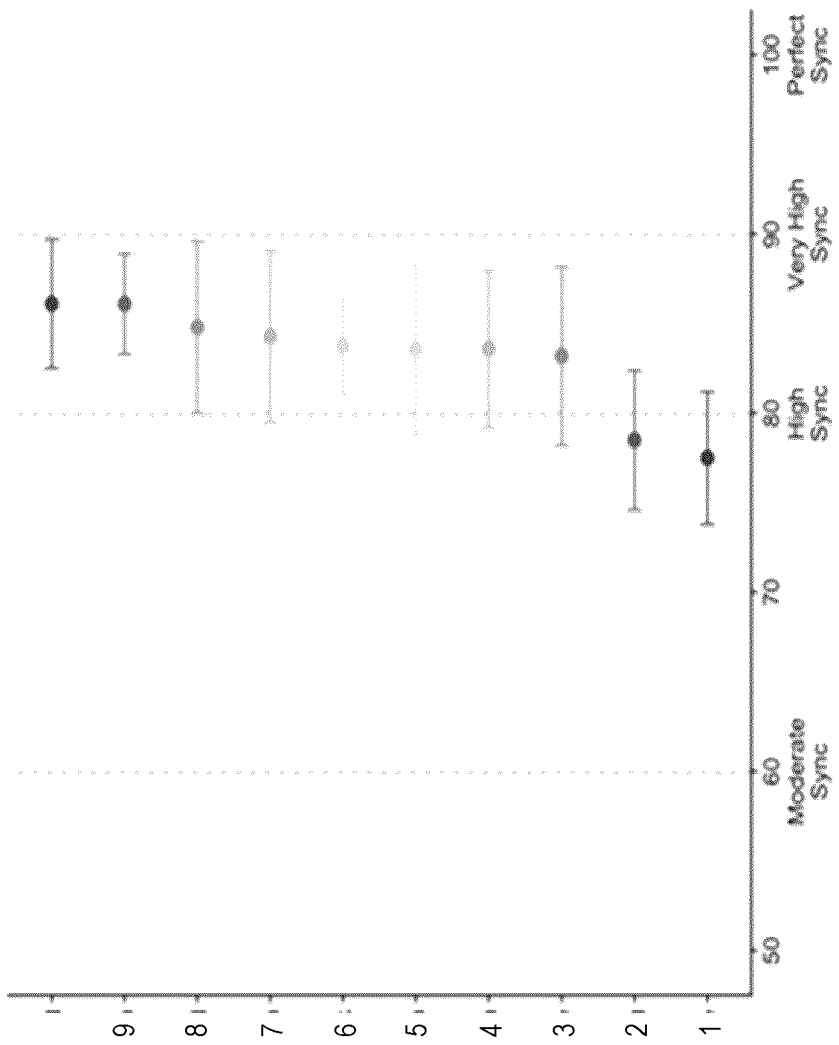
FIG. 6 shows mean and standard deviation of correlations between heart rates of 10 different participants in a 30-minute yoga class.

In various embodiments, the mean and standard deviation of the correlations for each user may be determined. For example, beat-to-beat heart rate files can be time-synchronized for all users and a normalized cross-correlation matrix is calculated to reflect the synchronicity in time-series correlation for all permutations of user connections. The mean and standard deviation of the correlations for each user may be determined. The mean and standard deviation may be scaled by, for example, multiplying or dividing the score so that it can fit within a scale before it is presented to the user. For example, the mean and standard deviation may be multiplied by 100 to give a score out of 100, or it can be multiplied by 10 to give a score out of 10. An example of this calculation for 10 users in a 30-minute yoga class where the physiological parameter is heart rate is shown in FIG. 6 as an example visualization that can be rendered on the interface 136. The hardware processor 112 transmits the emotional connectivity metrics to the interface 136 at a user device 130 in communication with the one or more servers 110 over the network 120 for data exchange. The user device 130 is programmed with executable instructions for generating the interface 136 with visual elements representing different levels of synchronicity of the users during the group activity. The different levels of synchronicity (very low, low, moderate, high, very high, perfect) can correspond to different connectivity values for user pairings or emotional connectivity metrics. The interface 136 provides improved visualizations corresponding to the emotional connectivity metrics. The improved interface 136 provides improved visualizations to indicate estimations of emotional connectivity and different levels of synchronicity for the group activity.

This calculation will show which users are most connected during the group activity and this data can be used to determine averages which reflect the emotional connectivity metric. An interface can render visualizations of the metrics to visually reflect the connectivity metrics for the group activity.

The server 110 can compute an emotion connectivity metric of a user relative to other participants of the group activity (i.e. based on average and the standard deviation), or relative to an absolute standard for the group activity or user, for example.

In various embodiments, the server 110 computes the emotional connectivity metric for each user in real time based on measured signals as they are received from the user devices 130. The emotional connectivity metrics are updated by the server 110 as more data are collected from the user devices 130. The server 110 can transmit emotional connectivity metrics to the user device 130 after it is re-computed based on update data collected from the user device 130. The user device 130 has an interface 136 that can display the emotional connectivity metrics to users via a display device with the displayed value being updated in real time based on data received from the server 110 to reflect the connectivity metric computations. The server 110 and the user device 130 can continue to exchange collected data and emotional connectivity metrics to continuously update the interface 136.

In various embodiments, the emotional connectivity metric for the group is calculated in real time based on measured signals as they are received from the user devices. The emotional connectivity metric is updated as server 110 collects more data. The emotional connectivity metric may be displayed to users via a display device with the displayed value being updated in real time.

In various embodiments, real-time values of the group connectivity metric may be used to create changes in the users' environment. This can be based on the group's average resilience metric or the average emotional fitness metric. For example, the intensity and color of lighting in a physical space may be changed as the group connectivity metric increase or decrease, or a sudden decrease in the group connectivity metric may trigger an audio device to begin playing calming sounds.

The server 110 can use the real-time values of the group connectivity metric to create changes in the users' environment by sending control commands to lighting, audio, temperature devices based on whether the connectivity metrics are higher or lower.

In some embodiments, two or more physiological parameters may be measured. A comparison can be performed of each of the measured signals, each representing a different physiological parameter of a user with the measured signals of one or more additional users. Signals representing the same physiological parameter can be compared with one another in order to calculate an emotional connectivity metric based on a weighted average of the synchronicity of each the measured signals.

In various embodiments, a cross-correlation matrix is calculated for each of the measured signals. The cross-correlations of each signal can be weighted and normalized to create a weighted cross-correlation matrix. This weighted cross-correlation matrix may be used in a same manner as a cross-correlation based on a single physiological parameter in calculating an emotional connectivity metric.

The server 110 can compute emotional fitness metrics and physical fitness metrics. The server 110 can compute emotional fitness metrics by defining rules for computing approximate values for environmental conditions, physical stress response to stimulus (body), and cognitive appraisal of the response (mind).

The server 110 can compute emotional fitness metrics over a time period for the group activity. The server 110 can compute different emotional fitness metrics over a time period for the group activity. The computed emotional fitness metrics over the time period for the group activity can indicate accumulation and progression of emotional fitness throughout the group activity. The server 110 can compute emotional fitness metrics by defining rules for computing approximate values for cognitive metrics for an appraisal of and reaction to environmental conditions and a response to triggers of the environmental conditions.

An example approximate value can be a mind function that receives situation metrics and body metrics as parameters for the server 110.

Emotional Fitness Metric=Mind(Situation*Body)

The server 110 can use data extracted from the measured signals to populate the parameters of the mind function to compute approximate values for emotional fitness metrics.

Another example approximate value for a cognitive metric that can be computed by server 110 is a user's resilience metric 350 that can involve a resiliency function with parameters. The resilience metric 350 can be used to compute approximate values for emotional fitness metrics.

Another example approximate value for a cognitive metric that can be computed by server 110 is a cognitive appraisal metric for each user or participant of the group activity.

The method may further comprise the server 110 determining the user's resilience metric 350 by measuring variability of the measured signal for the physiological parameter of the user over a time period of the group activity, requesting inputs from the interface 136 of the user's emotional state before 310) and after 330 performing the group activity and determining a cognitive appraisal metric based on the two emotional state inputs 360. In some embodiments, the server 110 determines the emotional fitness metric of the user based on the cognitive appraisal metric according to the example function 370:

Emotional Fitness Metric=Cognitive Appraisal(Emotional Connectivity Metric+Resilience Metric)

The example approximate value can be a cognitive appraisal function that receives emotional connectivity metrics and resiliency metrics as parameters for the server 110.

Another example function for server 110 to compute the cognitive appraisal metric is:

EFM=PerceptionDelta(Connection*Resilience)

whereby the perception delta score is >1 for positive shifts and scaled between 0 and 1 for negative shifts, therefore upweighting or downweighting the score driven by their in-class physical performance.

Figure 9:
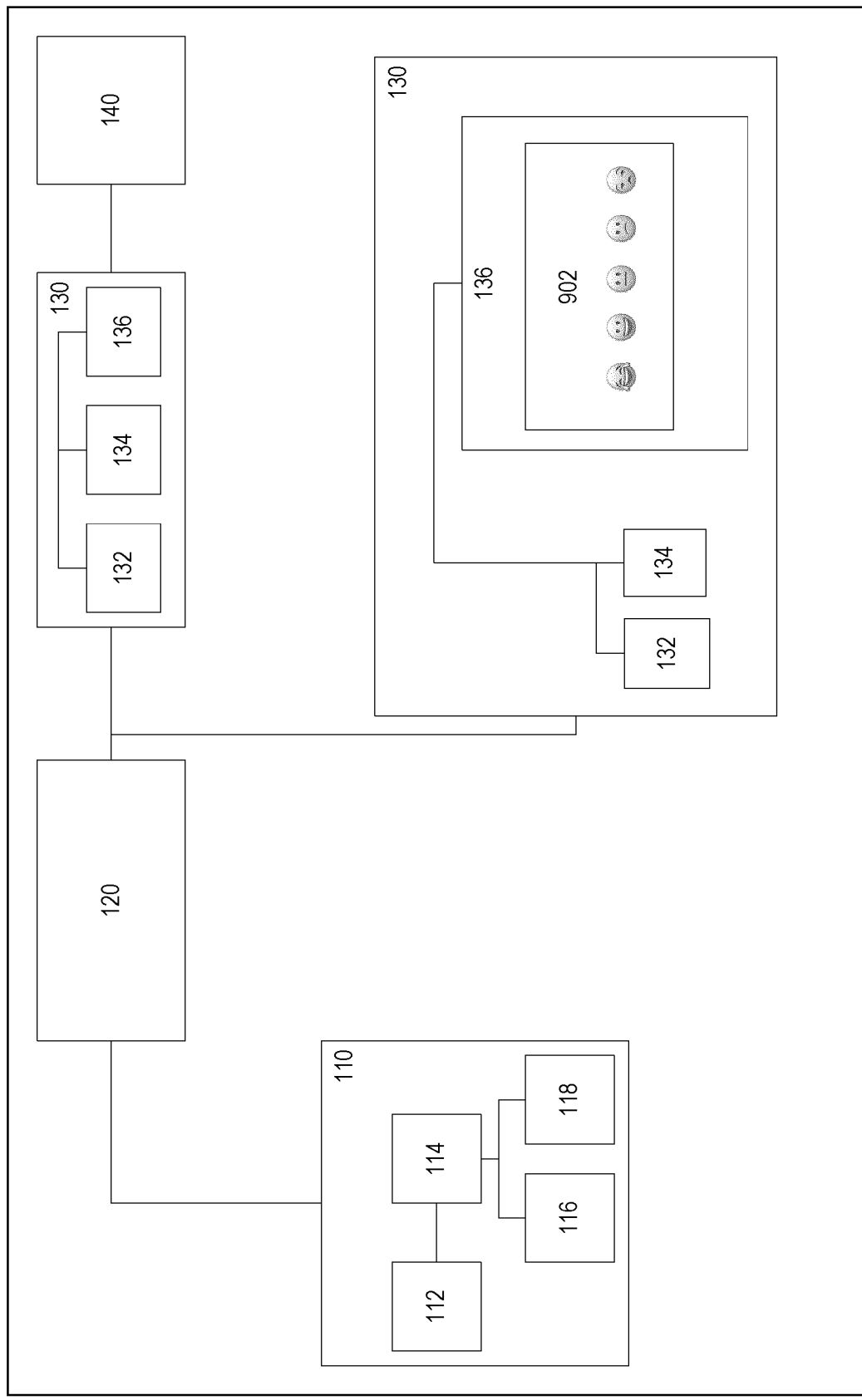
FIG. 9 shows an example interface of the system shown in FIG. 1.

FIG. 9 shows an example interface 136 (of the system shown in FIG. 1) with selectable indicia 902 to receive input data from users on different feeling states before, during, or after the group activity that can be used to quantify the perception delta score, as an example. The selectable indicia 902 correspond to different feeling states and the interface 136 can transmit the input data to server 110 over network 120 to compute delta metrics for the perception delta metrics used for the cognitive appraisal metrics.

The metrics could standalone as independent representations of aspects of emotional connectivity metrics, and the server 110 can match the metrics to intentional content creation to develop specific group activities deliberately designed to elevate each component of the functions or parameters used by the server 110, e.g. a 'Connection' class vs a 'Resilience' class. The content creation can map to different desired emotional states, for example, or different breath rates or breath rates to help increase connectivity for the group activity.

Emotional stability may be achieved through managing dynamic change. Thus, the resilience metric may be determined by combining the physical intensity achieved by the user with the variability in heart rate traces as a measure for how variable physiological challenge may build the resilience and emotional fitness needed for navigating the unpredictable demands and stressors of life. For example, during a yoga class, heart rate increases and decreases as users complete intense sequences of effort interspersed with intentional rest periods. Thus, a great amount of variability in the heart rate trace is achieved.

In various embodiments, the measured signal for the physiological parameter during the group activity is compared to the measured signal for the physiological parameter of the user at rest or when not performing the group activity. For example, if the physiological parameter is heart rate, the user's maximum heart rate for age and gender is considered in order to determine the user's "heart rate reserve".

The server 110 can receive input data for beat-to-beat heart rate files. The server 110 can clean the heart rate files, remove outliers, and time-sync the data for all participants of the group activity, as described herein in relation to the connection metric.

The server 110 can define personal heart rate parameters for each individual, in order to relativize their scores to their physiological baseline.

The server 110 can compute predicted maximum heart rate values.

A predicted maximum heart rate can be computed according to the formula:

Predicted Maximum Heart Rate=220−Age

The heart rate reserve is then calculated as the predicted maximum heart rate minus the minimum heart rate recorded during the group activity.

HeartRateReserve=PredictedMaximumHeartRate−MinimumHeartRateRecorded

This value represents the maximum fluctuation that may be expected for the user during the group activity.

The server 110 can compute or identify peaks in the heart rate curve. The peaks in the heart rate curve, defined as increases of 10% of the heart rate reserve over the preceding trough in the heart rate as an illustrative example, are then identified. For example, the server 110 can use parameters or thresholds to define fluctuations. An example parameter can be set as the number of occurrences when heart rate reaches 10% of the heart rate reserve or above which is preceded by a trough in heart rate. This value can be used to indicate that the user is in a state of physiological strain.

The server 110 can compute peak scale for the heart rate curve. For example, the server 110 can compute peak scale based on the following:

PeakScale=0.1×HeartRateReserve

The average peak height and number of peaks and troughs experienced by the user can be determined. The peak height is the difference in heart rate between a trough and a peak. The area under the curve of the heart rate measurements represents the work done by the user during the class, or physical effort expended relative to resting heart rate. The heart rate curve is shifted so that the lowest heart rate recorded is equal to zero in order to calculate the area under the curve. The resilience metric may then be calculated, for example, by the formula:

Resilience=Area Under Curve*(number of peaks*(Relative Mean Peak Height/Heart Rate Reserve)*100

The server 110 can compute data to relativize each heart rate reading to each individual's lowest recorded heart rate, in order to relativize area under the curve calculations:

HRDelta=CurrentHeartRate−MinimumHeartRateRecorded

The server 110 can sample data to collect observations for the data set.

An observation can indicate values for a time sample identifier, a time of day, a heart rate (bpm), participant identifier, a group activity type or group activity identifier, a minimum heart rate, a maximum heart rate, age data, predicted maximum, percentage of maximum, and so on.

The server 110 can calculate the area under the curve for each individual as an estimation or representation of "work done", or physical effort expended relative to resting heart rate.

The following example code snippet can be used by server 110 to compute the relative area under the curve for each individual:

```
get_AUC <- function(x) {
HR_Ind3 <- x
auc(HR_Ind3[[1]],HR_Ind3[[13]])/1000
}
AUC_Scores <- HR_Ind3 %>%
group_by(Participant) %>%
do(data.frame(AUC=get_AUC(.)))
```

The server 110 can compute and scale data values for the relative area under the curve and store in non-transitory memory as a pairing with a participant or user identifier.

The server 110 can compute the average peak height for each participant. The following example code snippet can be used by server 110 to compute the average peak height for each participant, including as peaks anything above 10% of their Heart Rate Reserve.

```
pk_height <- function (z) {
HR_Ind3 <- z
findpeaks(HR_Ind3[[13]],minpeakheight=HR_Ind3[[12]][[1]])
}
PkHeight <- HR_Ind3 %>%
group_by(Participant) %>%
do(data.frame(PkHeight=pk_height(.))) %>%
group_by(Participant) %>%
summarize(MeanPkHeight=mean(PkHeight.1))
```

The server 110 can compute and scale data values for the average heath rate peak height for each participant, and store in non-transitory memory as a pairing with a participant or user identifier.

The server 110 can compute the number of peaks experienced by each participant. The following example code snippet can be used by server 110 to compute the number of peaks experienced by each participant again including as peaks anything above 10% of their Heart Rate Reserve, with a minimum distance between unique peaks of 5 seconds:

```
get_npeaks <- function(y) {
HR_Ind3 <- y
nrow(findpeaks(HR_Ind3[[13]],minpeakheight=HR_Ind3[[12]][[1]],minpeakdistance=5))
}
NPeaks <- HR_Ind3 %>%
group_by(Participant) %>%
do(data.frame(NPeaks=get_npeaks(.)))
```

The server 110 can combine the data frames and calculate resilience using different functions of program instructions. For example, the server 110 can combine the data frames and calculate resiliency metrics using the following example function:

Resilience=AreaUnderCurve*PeakWeight

The server 110 can compute relative peak heights. For example, the peak height can be relativized to each participant's physiological range and multiplied by the number of peaks they achieved.

PeakWeight=NumberofPeaks*((MeanPeakHeight/HeartRateReserve)*100)

The following example code snippet can be used by server 110 to compute the relative peak heights.

```
Resiliency <- AUC_Scores %>%
left_join(NPeaks) %>%
left_join(PkHeight) %>%
left_join(HR_Min1) %>%
mutate(RelMeanPkHeight=(MeanPkHeight/HR_Reserve)*100) %>%
mutate(PeakWeight=(NPeaks*RelMeanPkHeight)/100,Resilience=AUC*PeakWeight) %>%
select(Participant,AUC,NPeaks,MeanPkHeight,RelMeanPkHeight,PeakWeight,Resilience)
%>%
mutate(Resilience=round(Resilience,0))
```

FIG. 7 shows the calculation of the resilience metric for a group of users.

In some embodiments, the server 110 determines a resilience metric based on variability of measured signals of physiological parameters of users acquired during a time period of a group activity. The interface 136 can generate visualizations corresponding to the resilience metrics for a group of users.

The example resilience metric for a group of users is based on heart rate data. For the heart rate example, the server 110 measures resiliency based on the heart rate reserve. The server 110 can use other types of user data to measure resiliency and can combine heart rate reserve with other types of signals and parameters to compute resiliency metrics. The heart rate reserve is a way to relativize the computation for individuals, knowing that everyone has a different resting heart rate and max heart rate as baseline or normal metrics. Using heart rate reserve allows the server to compute percentages to calculate and compare scores between individuals of the group activity.

The server 110 can compute variability using physical intensity and emotional fitness metrics. As noted, HRV is an example and the server 110 can compute the variability in time between each heartbeat. In some examples, the higher the score, the better an individual's emotional fitness is. Growth for users may come through supported change and challenge (variability) as compared to constancy, for example.

In some embodiments, the measured signals of the physiological parameters correspond to breathe rate traces, wherein the physiological parameter is a heart rate and the at least one biosensor is a breathe rate monitor. In some embodiments, the measured signals of the physiological parameters correspond to breath depth, and the at least one biosensor measures tidal volume. The server 110 can use breathe rate and breath depth to compute connectivity metrics.

The physiological parameters of a user can have relations to other physiological parameters of the user. For example, there can be a relationship between breathe depth or tidal volume and heart rate variability. An example relationship between these variables can be that breathing is the combination of how many times you breath per time period (e.g. minute), which can also be referred to as breathing rate, multiplied by the amount of air you breath in and out in each breath cycle (tidal volume, also referred to as breathing depth). The physiological parameters can be used as input variables for the server 110 to compute synchronicity and connection metrics. The server 110 can compute heart rate synchronicity for the connection metrics or breathing rate synchronicity for the connection metrics. The breathing depth can inform the resilience metric similar to how heart rate can be used for a measure of hard someone is working.

The methods as described herein further comprise requesting input from the user of an emotional state and/or recording an emotional state input into the memory both before 310 and after 330 performing the group activity. This input is requested on the basis that a user's reactions to and interpretation of physical responses can be used by the server 110 to determine emotional fitness. The emotional state input may comprise a numerical scale, an "emoji" input indicating a symbol, or other scaled input. If the user's emotional state improves as a result of the group activity, the user's emotional fitness metric is increased. If the user's emotional state decreases, then the cognitive appraisal is between 0 and 1 and the user's emotional state metric decreases. Charles et al. (2013, *Psychol. Sci.*, 24(5): 733-741) and Piazza et al. (2013, *Ann. Behav. Med.*, 45(1): 110-120) investigated the effects of exposure and affective response to daily stressors on the 10-year risk of individuals developing chronic health outcomes. Over 400 participants reported their amount of stress and negative affect at the end of each of eight consecutive days. Greater affective reactivity (essentially, the steeper the slope between self-reporting emotional valence and daily stress amount) was associated with substantially increased risk of developing chronic physical health conditions, likelihood of reporting affective disorders, and greater general affective distress when researchers followed up with participants 10 years later. Thus, associating increased physical stress with improved cognitive appraisal may be an indicator of higher emotional fitness.

The interface 136 (of the system shown in FIG. 1) can display different visual elements corresponding to computations for connectivity metrics, emotional fitness metrics, and resiliency metrics. The interface 136 can also collect input data for the computations by system.

The server 110 collects data from the connected user devices 130 for the group activity such as the measured signals of the physiological parameters of the users acquired by biosensors during the time period of the group activity over the network 120. The server 110 computes an emotional connectivity metric for the group activity to generate or update the interface 136 with visual elements derived based on the computations by the server 110 by processing the measured signals from the connected devices. The server 110 can identify measured signals of the physiological parameters of the users stored in the non-transitory memory using the group activity. The server 110 can time-synchronize the measured signals of the physiological parameters of the users. The server 110 compute a normalized cross-correlation matrix with connectivity values for user pairings for the group activity corresponding to a synchronicity in a time-series correlation for the physiological parameters for permutations of the user pairings for the group activity. For each user pairing of the permutations of user pairings for the group activity, the server 110 can compare the time-synchronized measured signals for the physiological parameters of a user of the respective user pairing to the time-synchronized measured signals for the physiological parameters of another user of the respective user pairing.

The server 110 can update the interface 136 with visual elements derived based on the connectivity values. The server 110 can transmit the connectivity values for the group activity to the interface 136 at the user device 130 in communication with the one or more servers 110 over the network 120 for data exchange and programmed with executable instructions for generating visual elements representing the connectivity values for the group activity. The server 110 can collect additional data and re-compute the connectivity values. The server 110 can trigger updates to the interface 136 based on the updated connectivity values. The interface 136 can update during the group activity, for example.

The server 110 can compute the emotional connectivity metrics for the group activity using the normalized cross-correlation matrix with the connectivity values for the user pairings for the group activity corresponding to the synchronicity in the time-series correlation for the physiological parameters for the permutations of the user pairings for the group activity. The server 110 can update the interface 136 with visual elements derived based on the emotional connectivity metrics. The server 110 can transmit the emotional connectivity metrics for the group activity to the interface 136 at the user device 130 in communication with the one or more servers 110 over the network 120 for data exchange and programmed with executable instructions for generating visual elements representing the emotional connectivity metric for the group activity and at least a portion of the connectivity values for the group activity.

FIG. 10 shows an example interface display for the system which can correspond to the example interface 136 shown in FIG. 1. The interface display can have a selectable indicia to trigger a command to start the computation process to generate visualizations.

FIG. 11 shows another example interface display for the system. The interface display can receive a user identifier as part of the process to generate visualizations for a group activity. The user identifier can be used to identify and collect records for the system.

Figure 12:
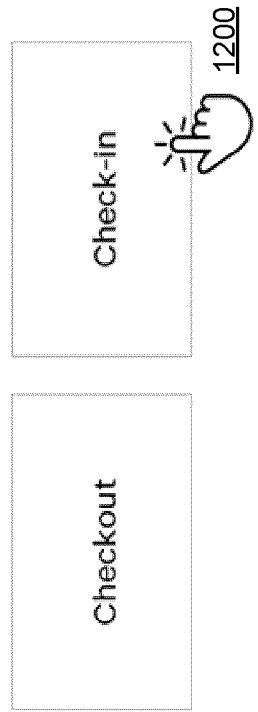
FIG. 12 shows another example interface diagram for the system.

FIG. 12 shows another example interface display for the system. The interface display can indicate a user identifier. The interface display can have a selectable indicia "check in" to trigger a command to start the computation process to generate visualizations for a group activity.

Figure 13:
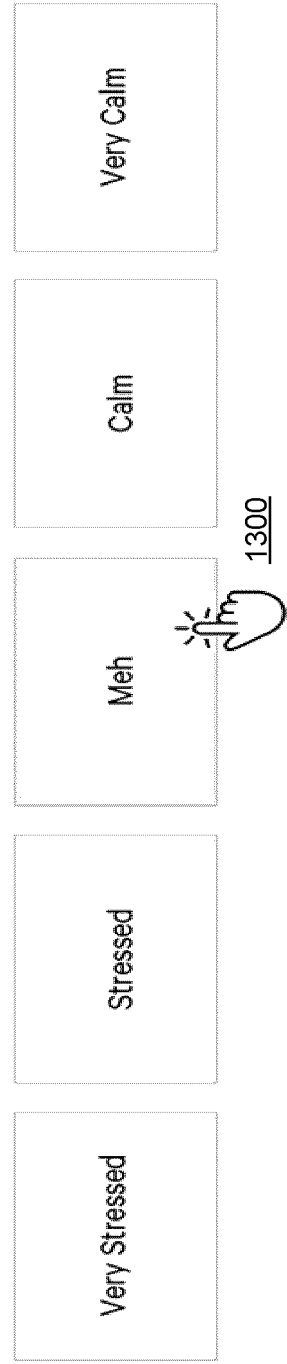
FIG. 13 shows another example interface diagram for the system.

FIG. 13 shows another example interface display for the system with selectable indicia 1300 to receive input data from users on different feeling states before, during, or after the group activity that can be used to quantify the perception delta score, as an example. The selectable indicia 1300 correspond to different feeling states. Selection at the interface display can trigger the interface 136 (FIG. 1) to transmit the input data to server 110 over network 120 to compute cognitive appraisal metrics.

Figure 14:
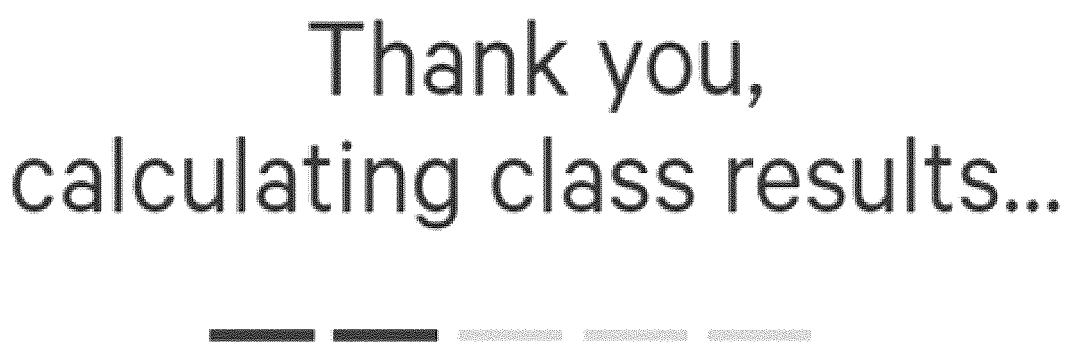

FIG. 14 shows another example interface display for the system during the real-time computation to generate metrics for the group activity in order to update the interface display in real-time for the group activity.

FIG. 15 shows another example interface display for the system relating to connectivity metrics which can be referred to as a connectedness view 1500. The interface display has different visual elements for the connectedness view 1500 that can be visually updated based on computations by the server 110 for the group activity. For example, the connectedness view 1500 can have a visual element for group connectivity 1502 with a corresponding displayed value or classification corresponding to the connectivity metrics and emotional fitness metrics computed by the server 110. The visual element for group connectivity 1502 can indicate an estimation for the overall group connectivity during the group activity. The server 110 can compute the estimation for the overall group connectivity during the group activity using the connectivity metrics. In this example, the visual element for group connectivity 1502 can indicate an estimated 'high sync' for the overall group connectivity during the group activity to indicate high levels of connectivity metrics.

The interface can display a combined visual element 1504 for the group activity that provides a combined visual display with a visual portion for connectivity metrics 1506, a visual portion for cognitive appraisal metrics 1510, and a visual portion for resiliency metrics 1508. The visual portion for connectivity metrics 1506 can visually indicate estimations for connectivity metrics. The interface can display a group event element 1512 that represents connectivity metrics for different events for the group activity. The different events can correspond to different time frames during the group activity or different physiological values. In this example, the events correspond to different poses during a yoga class and the group event element 1512 has different visual elements corresponding to different events for the group activity to visually indicate estimations for connectivity metrics for the different events.

FIG. 16 shows another example interface display for the system relating to resiliency metrics which can be referred to as a resiliency view 1600. The server 110 can compute 'resiliency metrics' using connectivity metrics. The interface display has different visual elements for the resiliency view 1600 that can be visually updated based on computations by the server 110 for the group activity. For example, the resiliency view 1600 can have a visual element for group resiliency 1602 with a corresponding displayed value or classification corresponding to the resiliency metrics computed by the server 110. The visual element for group resiliency 1602 can indicate an estimation for the overall group resiliency during the group activity. The server 110 can compute the estimation for the overall group resiliency during the group activity using the resiliency metrics. In this example, the visual element for group resiliency 1602 can indicate an estimated 'excellent' value for the overall group resiliency during the group activity to indicate high levels of resiliency metrics.

The interface with the resiliency view 1600 can display a combined visual element 1504 for the group activity that provides a combined visual display with a visual portion for connectivity metrics 1506, a visual portion for emotional fitness metrics 1510, and a visual portion for resiliency metrics 1508. The visual portion for resiliency metrics 1508 can visually indicate estimations for resiliency metrics. The interface can display a group resiliency event element 1612 that represents resiliency metrics for different events for the group activity. The different events can correspond to different time frames during the group activity or different physiological values. In this example, the events correspond to different poses during a yoga class and the group event element 1612 has different visual elements corresponding to different events for the group activity to visually indicate estimations for heart rates and resiliency metrics for the different events.

FIG. 17 shows another example interface display for the system relating to cognitive appraisal metrics which can be referred to as a cognitive appraisal view 1700.

The server 110 can compute 'cognitive appraisal metrics' using connectivity metrics and emotion state input. The interface display has different visual elements for the cognitive appraisal view 1700 that can be visually updated based on computations by the server 110 for the group activity. For example, the cognitive appraisal view 1700 can have a visual element for group cognitive appraisal 1702 with a corresponding displayed value or classification corresponding to the cognitive appraisal metrics computed by the server 110. The visual element for group cognitive appraisal 1702 can indicate an estimation for the overall group resiliency during the group activity. The server 110 can compute the estimation for the overall group resiliency during the group activity using the resiliency metrics. In this example, the visual element for group resiliency 1602 can indicate an estimated 'positive' value for the overall group cognitive appraisal during the group activity to indicate positive cognitive appraisal metrics.

The interface with the cognitive appraisal view 1700 can display a combined visual element 1504 for the group activity that provides a combined visual display with a visual portion for connectivity metrics 1506, a visual portion for cognitive appraisal metrics 1510, and a visual portion for resiliency metrics 1508. The visual portion for cognitive appraisal metrics 1510 can visually indicate estimations for cognitive appraisal metrics. The interface can display a cognitive appraisal change element 1712 that represents cognitive appraisal metrics for different events for the group activity. The different events can correspond to different time frames during the group activity or different physiological values. In this example, the events correspond to a time before and after the group activity and the group cognitive appraisal change element 1712 has different visual elements corresponding to estimations for cognitive appraisal metrics before, during and after the group activity to show the change in the cognitive appraisal for the group activity.

Figure 18:
FIG. 18 shows another example interface diagram for the system.

FIG. 18 shows another example interface display for the system relating to emotional fitness metrics which can be referred to as the emotional fitness view 1800.

The server 110 can compute 'emotional fitness metrics' using connectivity metrics. The interface display has different visual elements for the emotional fitness view 1800 that can be visually updated based on computations by the server 110 for the group activity. For example, the emotional fitness view 1800 can have a visual element for overall emotional fitness 1802 for the user for the group activity with a corresponding displayed value or classification corresponding to the emotional fitness metrics computed by the server 110. The visual element for the overall emotional fitness 1802 can indicate an estimation for the overall emotional fitness during the group activity. The server 110 can compute the estimation for the overall emotional fitness during the group activity using the emotional fitness metrics during the time period for the activity. In this example, the visual element for the overall emotional fitness 1802 can indicate an estimated value 4.1 of a total possible of 5 for the group activity to indicate the emotional fitness metrics. The emotional fitness view 1800 can indicate a change in the overall emotional fitness 1802 since the last group activity for the user, for example, to indicate an increase or decrease in the emotional fitness metrics for the user.

The interface with the emotional fitness view 1800 can display a combined visual element 1504 for the group activity that provides a combined visual display with a visual portion for connectivity metrics 1506, a visual portion for cognitive appraisal metrics 1510, and a visual portion for resiliency metrics 1508 to show a visual connection between the overall emotional fitness 1802 and the other metrics.

Figure 19:
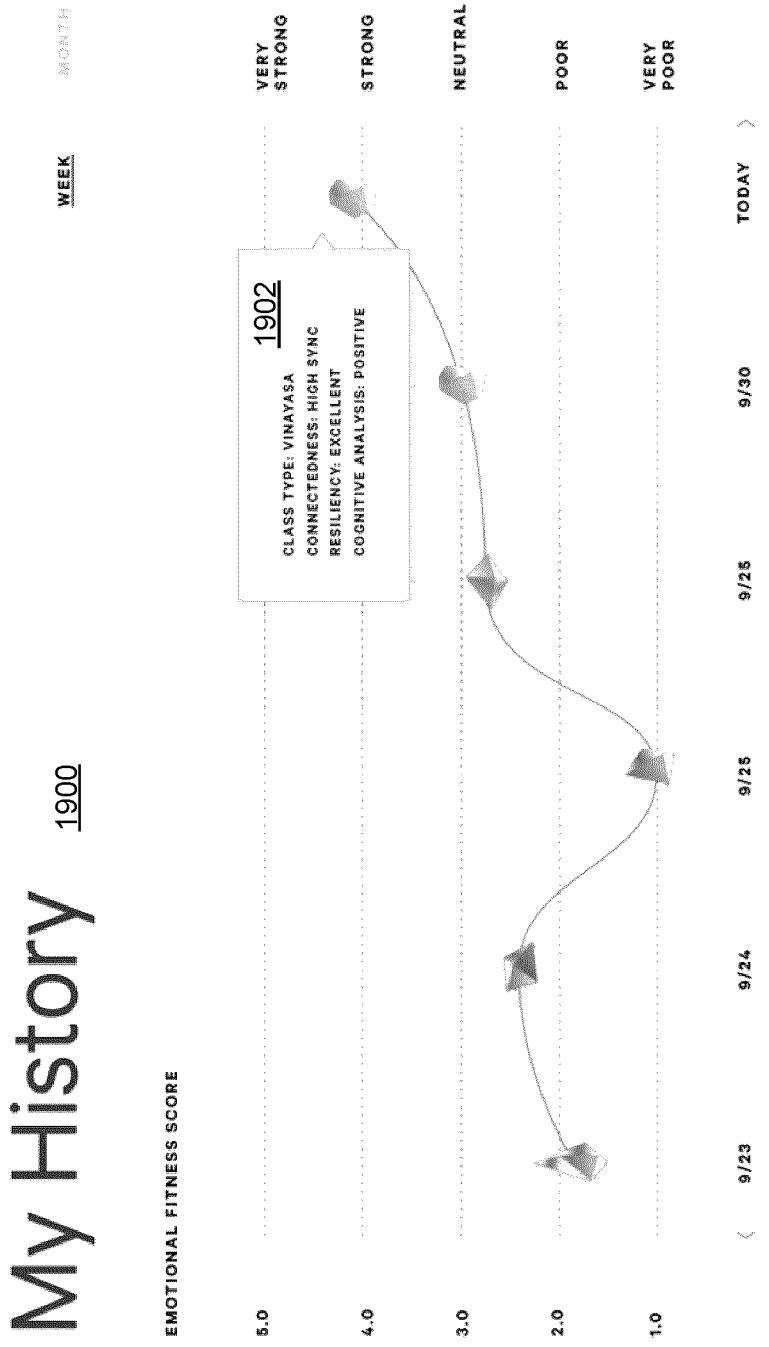
FIG. 19 shows another example interface diagram for the system.

FIG. 19 shows another example interface display for the system relating to emotional fitness metrics for different group activities over time which can be referred to as the emotional fitness history view 1900. A visual element can include a graph that indicates different overall emotional fitness metrics for different group activities to show relative emotional fitness metrics for the different group activities. The emotional fitness history view 1900 can indicate group activity summary 1902 to indicate group activity type, an overall connectivity metric, an overall resiliency metric, and an overall cognitive appraisal metrics.

The example interface displays provide improved visualizations of the raw data collected during the group activity. The interface displays can be provided by interface 136 shown in FIG. 1 to provide improved computer visualizations. In some example embodiments, the interface displays are continuously updated in real-time in response to the server 110 continuously computing updated metrics from new data collected for the group activity. The interface can having moving portions (e.g. circles or shapes) representing different users of the group activity that can change color and location as the metrics are computed by server 110. The size of the portions for different users can also change based on the metrics computed by server 110.

Figure 8:
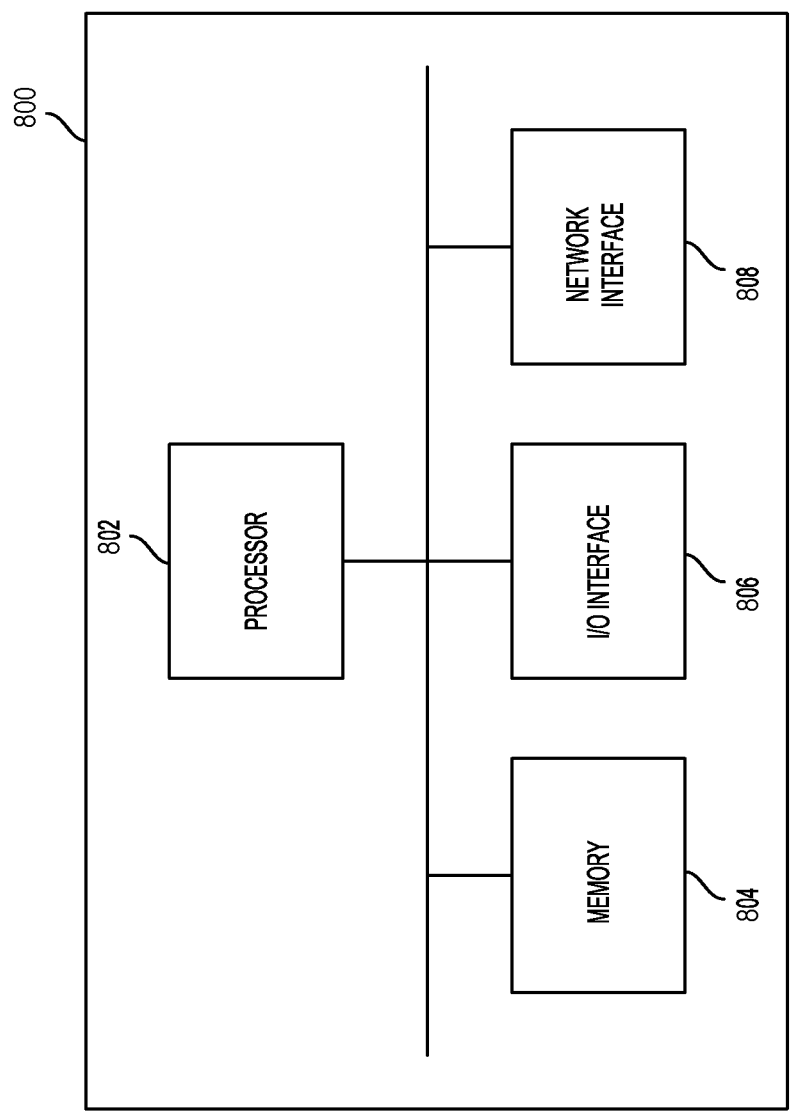
FIG. 8 shows an example computer device.

FIG. 8 is a schematic diagram of a computing device 800 that can implement aspects of embodiments. As depicted, the display device 800 includes at least one processor 802, non-transitory memory 804, and at least one I/O interface 806, and at least one network interface 808.

The emotional state inputs may be provided on an I/O interface 806 of the device 800. The I/O interface 806 can include software and hardware configured to facilitate communications with the hardware processor 802 and/or communications to the user. The hardware includes a display screen configured to visually display graphics, text and other data to the user. In various embodiments, the hardware processor 802 is configured to request the inputs from the user to be entered on the display device.

The memory 804 is configured to store information, including both data and instructions. The data generally include the measured signal for the physiological parameter, the emotional state inputs that may be retrieved from the processing unit, along with other data that may be ancillary to the basic operation of the processing unit. In various embodiments, the memory 804 may store any data of measured signals for the physiological parameter and/or emotional state inputs inputted by the user previously.

The instructions which are stored at the memory 804 generally include firmware and/or software for execution by the hardware processor 802, such as a program that controls the settings for the at least one biosensor 140, a program that controls the processing of the data from the at least one biosensor 140 to determine the measured signal, a program that associates the measured signal to a time stamp, a program that compares the measured signal of the physiological parameter of the user with the measured signal of the physiological parameter for the one or more additional users, one or more programs for calculating the emotional connectivity metric based on the synchronicity of the measured signal for the physiological parameter of the user with the measured signal of the physiological parameter of the one or more additional users, one or more programs for calculating the resilience metric, a program that requests input from the user of an emotional state before and after performing the group activity, a program that controls the processing of the emotional state of the user to determine the cognitive appraisal metric, a program that controls the transmission and reception of data from the at least one biosensor, a program that determines an emotional fitness metric from the cognitive appraisal metric, emotional connectivity metric and resilience metric, as well as any of various other programs that may be associated with the system. The program can control components of the user device 130. The program can control components of the server 110, as another example. In various embodiments, two or more of the foregoing may be combined into one program or distributed across multiple programs and can be linked or connected.

The memory 804 may be of any type of device (or combination of devices) capable of storing information accessible by the hardware processor 802, such as a memory card, ROM, RAM, write-capable memories, read-only memories, hard drives, discs, flash memory, or any of various other computer-readable media serving as data storage devices as known by a person of ordinary skill in the art. The data may also be formatted in any computer-readable format such as, but not limited to, binary values, ASCII or Unicode.

The hardware processor 802 may be in communication with or part of a display device configured to display the emotional fitness metric to the user and provide recommendations to the user of activities for improving the emotional fitness metric.

In various embodiments, the display device may be a standalone device such as a desktop PC or smart television or any type of portable or other personal electronic device such as a smartphone, tablet computer, laptop computer, smartwatch, or any of various other mobile computing devices. As will be recognized by one of ordinary skill in the art, the components of the display device may vary depending on the type of display device used. The display device generally includes an input/output interface, the processing unit, and a memory.

In various embodiments, the display screen of device 800 is configured to display an interface with the emotional fitness metric received from the hardware processor 802. The hardware may also include a microphone and/or speakers to facilitate audio communications with the user and/or verbal entry of commands to the device 800. In various embodiments, the display screen is a touch screen display that allows the user to see data of the interface presented on the display screen and input data into the display device via a keyboard on the touch screen.

The hardware processor 802 is connected to the I/O interface 806, and the memory 804, and is configured to deliver data to and/or receive data from each of these components. In various embodiments, the hardware processor 802 is configured to process data received from the at least one biosensor 130 (for example, via the transceiver) and the I/O interface 806 and transform the data into a graphical format for presentation on the display screen. As understood by a person of ordinary skill in the art, a "processing unit" as used herein includes any hardware system, hardware mechanism or hardware component that processes data, signals or other information. A hardware processor 802 can include a system with a central processing unit, multiple processing units, dedicated circuitry for achieving functionality, or other systems.

In at least one embodiment, portions of the system and methods described herein may be implemented in suitable software code that may reside within the memory. Such software code may be present on the device 800 or hardware processor 802 at the time of manufacture or may be downloaded thereto via well-known mechanisms. A computer program product implementing an embodiment disclosed herein may therefore comprise one or more computer-readable storage media storing computer instructions translatable by a processing unit, processor or microprocessor to provide an embodiment of a system or perform an embodiment of a method disclosed herein. Computer instructions may be provided by lines of code in any of various languages as will be recognized by those of ordinary skill in the art. A "computer-readable medium" may be any type of data storage medium that can store computer instructions, including, but not limited to, the memory devices discussed above. Computer instructions can also be provided by lines of code in any of various languages as will be recognized by those of ordinary skill in the art.

The device 800 also includes a battery or other power source configured to power the various electronic components within the display device.

The emotional fitness metric may be processed and displayed on the device 800 using the software application or "app" stored in a computer readable medium such as the memory 804 of the device. The hardware processor 802 of the device 800 is configured to process the instructions for the app. The processing unit may be controlled by computer-executable instructions stored in the memory so as to provide the functionality as is described herein. For example, the hardware processor 802 may process the emotional connectivity metric, the cognitive appraisal and/or the resilience metric in order to present the emotional fitness metric in a format for an interface that communicates the data to the user. The device 800 includes a display screen configured to display the processed data.

In various embodiments, a non-transient computer readable medium contains instructions for controlling the device 800 by receiving emotional fitness metric data from the hardware processor 802 (or server 110) and presenting the emotional fitness metric to the user on the display device.

In various embodiments, the methods disclosed herein provide a recommendation or coaching for improving the emotional fitness metric of the user. The methods disclosed herein are based on combining physiological measurements and emotional data for the user to provide recommendations for promoting emotional fitness to increase feelings of wellness for the user. For example, the user may be recommended to attend a fitness class with others for which the user had the highest connectivity. Alternatively, the user may be recommended to attend classes or sessions which aim to improve resilience or cognitive appraisal.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

The invention claimed is:

1. A computer hardware system for capturing and processing measured signals of physiological parameters of users acquired during a time period of a group activity, the system comprising:

non-transitory memory to receive and store measured signals of physiological parameters of users acquired during the time period of the group activity from a network;

at least one biosensor to acquire a measured signal of a physiological parameter of a user during the time period of the group activity and having a transmitter to transmit the measured signal of the physiological parameters of the user acquired during the time period of the group activity over the network;

one or more servers having a hardware processor coupled to the memory to access the measured signals of physiological parameters of the users acquired during the time period of the group activity to compute at least one metric for the group activity, wherein the group activity involves a set of users that are paired into different permutations of user pairings to compute the at least one metric for the group activity, the hardware processor executing instructions stored in the memory to:

identify measured signals of the physiological parameters of the users stored in the non-transitory memory using the group activity;

time-synchronize the measured signals of the physiological parameters of the users;

compute a normalized cross-correlation matrix with connectivity values for the different permutations of user pairings for the group activity, the connectivity values providing estimations for synchronicity of the time-synchronized measured signals for the physiological parameters for the different permutations of the user pairings for the group activity, wherein the hardware processor computes multiple dimensions of connectivity values for each user pairing of the different permutations of user pairings for the group activity comparing the time-synchronized measured signals for a plurality of the physiological parameters of a user of the respective user pairing to the time-synchronized measured signals for the plurality of the physiological parameters of another user of the respective user pairing, wherein the hardware processor uses the different permutations of the user pairings to compare the time-synchronized measured signals for the physiological parameters of the users; and compute the at least one metric for the group activity using the normalized cross-correlation matrix with the connectivity values for the user pairings for the group activity corresponding to the synchronicity of the time-synchronized measured signals for the physiological parameters for the different permutations of the user pairings for the group activity, wherein the at least one metric for the group activity indicates estimations of connectivity between users of the group activity; and transmit at least a portion of the connectivity values for the user pairings for the group activity and the at least one metric for the group activity to an interface at a computing device in communication with the one or more servers over the network for data exchange and programmed with executable instructions for generating visual elements representing the at least one metric for the group activity and the at least a portion of the connectivity values for the user pairings for the group activity;

wherein the interface at the computing device receives control commands and data to automatically update to visually indicate the visual elements representing the at least one metric for the group activity and the portion of the connectivity values for the user pairings for the group activity to indicate the estimations of connectivity between the users of the group activity.

2. The system of claim 1 wherein the one or more servers use the connectivity values for the user pairings to identify a user pairing having a strong connectivity value for the group activity for the permutations of the user pairings for the group activity, wherein the interface visually indicates the user pairing having the strong connectivity value for the group activity.

3. The system of claim 1 wherein the one or more servers computes an overall group connectivity score for the group activity by calculating a group average of the connectivity values for the user pairings corresponding to the synchronicity in the time-series correlation for the physiological parameters for the permutations of the user pairings for the group activity, wherein the interface visually indicates the overall group connectivity score.

4. The system of claim 1 wherein the one or more servers clean and remove outliers from the measured signals of the physiological parameters of the users acquired during the time period of the group activity prior to the time-synchronize using an standard outlier filter to automatically remove any data points that are outside of a number of standard deviations from a group average.

5. The system of claim 1 wherein the measured signals of the physiological parameters correspond to heart rate traces, wherein the physiological parameter is a heart rate and the at least one biosensor is a heart rate monitor.

6. The system of claim 1 wherein the one or more servers compute, based on the measured signals of the physiological parameters of the users, a variability of a physiological parameter of a user and determines a resilience metric for the user based on such variability in the physiological parameter, wherein the interface visually indicates the resilience metric for the user.

7. The system of claim 6, wherein the physiological parameter is a heart rate and the at least one biosensor is a heart rate monitor, wherein the variability of the physiological parameter is calculated by calculating a number of peaks and troughs in a heart rate curve, and wherein the calculating comprises counting and weighting the peaks and troughs in the heart rate curve.

8. The system of claim 1 wherein the one or more servers computes the at least one metric for the group activity based on correlation with additional metrics for the group activity.

9. The system of claim 1, wherein the one or more servers computes the at least one metric for the group activity after additional users have performed and completed the group activity and recorded their physiological parameter in a database, wherein the one or more servers compares the physiological parameter of the user with the physiological parameters recorded in the database.

10. The system of claim 1 further comprising one or more additional group devices in communication with the one or more servers over the network to receive control commands based on the at least one metric for the group activity during the time period for the group activity.

\* \* \* \* \*